(12) United States Patent
Hu et al.

(10) Patent No.: US 11,912,643 B2
(45) Date of Patent: Feb. 27, 2024

(54) LIQUID-SOLID AXIAL MOVING BED REACTION AND REGENERATION DEVICE, AND SOLID ACID ALKYLATION METHOD

(71) Applicants: CHINA PETROLEUM & CHEMICAL CORPORATION, Beijing (CN); RESEARCH INSTITUTE OF PETROLEUM PROCESSING, SINOPEC, Beijing (CN)

(72) Inventors: Lifeng Hu, Beijing (CN); Shuandi Hou, Beijing (CN); Junyi Mao, Beijing (CN); Zhenxing Zhu, Beijing (CN); Xiaojin Tang, Beijing (CN); Zheng Liu, Beijing (CN); Yongxiang Li, Beijing (CN); Zhihai Zhao, Beijing (CN)

(73) Assignees: CHINA PETROLEUM & CHEMICAL CORPORATION, Beijing (CN); RESEARCH INSTITUTE OF PETROLEUM PROCESSING, SINOPEC, Beijing (CN)

( * ) Notice: Subject to any disclaimer, the term of this patent is extended or adjusted under 35 U.S.C. 154(b) by 357 days.

(21) Appl. No.: 17/287,648

(22) PCT Filed: Oct. 22, 2019

(86) PCT No.: PCT/CN2019/112517
§ 371 (c)(1),
(2) Date: Apr. 22, 2021

(87) PCT Pub. No.: WO2020/083279
PCT Pub. Date: Apr. 30, 2020

(65) Prior Publication Data
US 2021/0395167 A1 Dec. 23, 2021

(30) Foreign Application Priority Data

Oct. 22, 2018 (CN) .......................... 201811229732.2
Oct. 22, 2018 (CN) .......................... 201811230209.1

(51) Int. Cl.
*C07C 2/62* (2006.01)
*B01J 8/12* (2006.01)
(Continued)

(52) U.S. Cl.
CPC ................. *C07C 2/62* (2013.01); *B01J 8/125* (2013.01); *B01J 29/084* (2013.01); *B01J 38/56* (2013.01);
(Continued)

(58) Field of Classification Search
CPC ......... C07C 2/62; C07C 2/58; C07C 2529/08; B01J 8/125; B01J 29/084; B01J 38/56;
(Continued)

(56) References Cited

U.S. PATENT DOCUMENTS 2,656,007 A 10/1953 Erich et al.
4,446,112 A 5/1984 Den Hartog
(Continued)

FOREIGN PATENT DOCUMENTS

CN 1113906 A 12/1995
CN 1879956 A 12/2006
(Continued)

OTHER PUBLICATIONS

International Search Report of International Application No. PCT/CN2019/112517, dated Jan. 19, 2020.

*Primary Examiner* — Thuan D Dang
(74) *Attorney, Agent, or Firm* — Finnegan Henderson Farabow Garrett & Dunner LLP

(57) ABSTRACT

A liquid-solid axial moving bed reaction and regeneration apparatus and a solid acid alkylation process by using the
(Continued)

liquid-solid axial moving bed reaction and regeneration apparatus. the liquid-solid axial moving bed reaction and regeneration apparatus comprise:

An axial moving bed reactor (1), a spent catalyst receiver (5), a catalyst regenerator (4) and a regenerated catalyst receiver (6) that are successively connected, wherein, a catalyst outlet of the regenerated catalyst receiver (6) is communicated with a catalyst inlet of the axial moving bed reactor (1);

Wherein, the axial moving bed reactor (1) is provided with at least two catalyst beds (3) arranged up and down, the axial moving bed reactor (1) is provided with a feed inlet (2) above each catalyst bed (3);

A catalyst delivery pipe (16) is arranged between two adjacent catalyst beds (3) so that the catalyst can move from top to bottom in the axial moving bed reactor (1);

A separation component (10) is provided between two adjacent catalyst beds (3), the inside space of the separation component (10) is communicated with the catalyst delivery pipe (16), the separation component (10) is for separating the stream after the reaction in the upstream catalyst bed from the catalyst, the catalyst obtained by the separation with the separation component (10) moves down through the catalyst delivery pipe (16).

36 Claims, 4 Drawing Sheets

(51) Int. Cl.
*B01J 29/08* (2006.01)
*B01J 38/56* (2006.01)
*C10G 50/00* (2006.01)

(52) U.S. Cl.
CPC ...... *C10G 50/00* (2013.01); *B01J 2208/00929* (2013.01); *C10G 2300/305* (2013.01); *C10G 2300/4006* (2013.01); *C10G 2300/4012* (2013.01); *C10G 2300/4018* (2013.01); *C10G 2300/70* (2013.01)

(58) Field of Classification Search
CPC .............. B01J 2208/00929; B01J 8/085; B01J 2208/00849; B01J 2208/00938; C10G 50/00; C10G 2300/305; C10G 2300/4006; C10G 2300/4012; C10G 2300/4018; C10G 2300/70; C10G 29/205
See application file for complete search history.

(56) References Cited

U.S. PATENT DOCUMENTS

| | | | |
|---|---|---|---|
| 5,567,396 A | | 10/1996 | Perry et al. |
| 5,849,976 A | * | 12/1998 | Gosling .................... B01J 8/12 585/709 |
| 8,373,014 B2 | | 2/2013 | Sadler et al. |
| 2011/0152950 A1 | | 6/2011 | Baccelli |
| 2012/0094364 A1 | | 4/2012 | Lali et al. |
| 2018/0117580 A1 | | 5/2018 | Grott et al. |

FOREIGN PATENT DOCUMENTS

| | | |
|---|---|---|
| CN | 102485840 A | 6/2012 |
| CN | 105441116 A | 3/2016 |
| CN | 106622040 A | 5/2017 |
| WO | WO 2012/167708 A1 | 12/2012 |

* cited by examiner

LIQUID-SOLID AXIAL MOVING BED REACTION AND REGENERATION DEVICE, AND SOLID ACID ALKYLATION METHOD

CROSS-REFERENCE TO RELATED APPLICATIONS

This application is a national stage filing under 35 U.S.C. § 371 of International Application No. PCT/CN2019/112517, filed Oct. 22, 2019, which claims the priority to and benefits of Chinese Patent Application Nos. 201811229732.2 and 201811230209.1, filed Oct. 22, 2018, which are both incorporated herein by reference in their entireties.

TECHNICAL FIELD

The present invention relates to the field of solid acid alkylation. In particular, the present invention relates to a liquid-solid axial moving bed reaction and regeneration apparatus, and a solid acid alkylation process.

BACKGROUND TECHNOLOGY

At present, one of the most important tasks of the oil refining industry is to provide transportation fuel. As an important transportation fuel, gasoline is widely used in communication and transportation and other industries. With the increase in gasoline consumption and increasingly strict environmental protection standards, how to solve the problem of clean gasoline production has become a hot topic of research and discussion.

Under the action of strong acid, the technology of using isoparaffins (mainly isobutane) and alkenes (C3-C5 alkenes) as raw materials to produce an alkylation oil provides the possibility for the clean production of gasoline. The alkylation oil has a high octane number and a low vapor pressure. It is mainly composed of saturated hydrocarbons and does not contain sulfur, nitrogen, alkenes, aromatics and the like. Therefore, it is called a cleaned gasoline and is an ideal blending component for aviation gasoline and motor gasoline. Alkylation technology can be divided into liquid acid alkylation and solid acid alkylation according to the catalyst form. At present, about 90% of the world alkylation capacity is provided by the liquid acid alkylation technology (sulfuric acid process and hydrofluoric acid process), although the liquid acid alkylation technology is relatively mature and has better reaction selectivity, however, there are many problems. For example, the liquid acid alkylation process has serious equipment corrosion problems. In addition, for the sulfuric acid process, this process consumes a large amount of the acid, and a large amount of waste acid has certain safety hazards in transportation and disposal. For the hydrofluoric acid process, because hydrofluoric acid has strong causticity and toxicity and is easily volatile, this process can cause great harm to the human body. Therefore, in contrast, using a solid acid as the catalyst not only does not cause pollution to the environment, but also does not have the problem of equipment corrosion. It can be regarded as a green alkylation technology with good development prospects. However, in the solid acid alkylation process, since the solid acid catalyst is easy to deactivate, in order to maintain a certain reaction activity, frequent regeneration operations are required. Therefore, the development of the reactor technology that can realize the continuous reaction and regeneration is very important to promote the development of solid acid alkylation technology.

U.S. Pat. No. 8,373,014 discloses a solid acid alkylation reaction process using the radial moving beds that are overlapped each other as the reactor. In this process, a structure similar to the overlapping radial moving bed for catalytic reforming is adopted. The single-stage reactor is provided with an annular barrel for distributing the reaction streams on the periphery and a central tube for collecting the streams and the reaction bed zone sandwiched between the two; the catalyst stream delivery pipe is used between the two reactors to transport the catalyst in the upper catalyst bed to the reaction bed zone of the lower reactor. The effluent stream in the intermediate reactor is divided into two parts. One part is pumped back to the upstream reactor and mixed with the fresh reaction feedstock as the feed of the upstream reactor after being mixed with the mixer. This part can be called the recycled stream. The other part is mixed with the fresh reaction feedstock and then introduced into the feed mixer of the downstream reactor as the feed to the downstream reactor, and this part is directly used without pump pressurization. In addition, a part of the recycled stream needs to pass through a heat exchanger to take out the reaction heat.

CN1879956A discloses a fluidized bed solid acid alkylation technology, which mainly includes a riser reactor, a fluidized bed reactor, a circulation flow regenerator and a moving bed regenerator. Among others, the liquid velocity in the riser reactor is 0.1-3 m/s, the liquid velocity in the fluidized bed reactor is 0.26-7.68 cm/s. For the regeneration process, the form of the regeneration reactor can be determined according to the regeneration time. If the regeneration time is from a few seconds to several tens of seconds, a circulation flow regenerator can be used alone. If the regeneration time is from tens of seconds to tens of minutes, a moving bed regenerator can be used alone, and the liquid velocity of the regeneration liquid 0.2-3 cm/s.

CN1113906A discloses a fluidized bed solid acid aromatic hydrocarbon alkylation technology. The technology mainly includes a liquid-solid upward reactor, a spent catalyst sedimentation backwash column, a liquid-solid cocurrent flow upward regenerator, and a regenerated catalyst sedimentation backwash column. Among others, the particle size of the catalyst used according to the requirements is 0.05-0.8 mm, the liquid velocity of the liquid that can carry the catalyst to flow upward in the reactor and the regenerator is 1-15 times the particle terminal settling velocity. In the sedimentation backwash column, the catalyst is washed with a washing liquor flowing from bottom to top and regenerated, and the flow velocity of the washing liquor is 0.5-5 times the particle terminal settling velocity.

The fixed bed alkylation technology and the fluidized bed alkylation technology disclosed in the prior art require at least two or more reactors to switch operations in order to realize the continuous and stable operation of the reaction apparatus, and the catalyst in the bed is subjected to high temperature regeneration at regular intervals, and after deep regeneration, the high-temperature bed needs to be cooled down. Because the apparatus is frequently switched between the reaction temperature and the regeneration temperature, it causes many problems during continuous and stable operation in industrial applications. In addition, in the prior art, it is difficult for the catalyst in the solid acid alkylation reaction apparatus to maintain a stable and high target product selectivity.

SUMMARY OF THE INVENTION

In order to overcome the problem that the solid acid alkylation reaction in the prior art cannot operate continuously and stably, and the selectivity of the target product needs to be further improved, the present invention provides a solid acid alkylation process. Using the process provided by the present invention not only can realize the continuous and stable operation of the solid acid alkylation reaction, but also can improve the selectivity of the target product.

In order to achieve the above objectives, the present invention provides the following technical solutions:

1. A liquid-solid axial moving bed reaction and regeneration apparatus, which is characterized in that the apparatus comprises:

An axial moving bed reactor (1), a spent catalyst receiver (5), a catalyst regenerator (4) and a regenerated catalyst receiver (6) that are successively connected, wherein, a catalyst outlet of the regenerated catalyst receiver (6) is communicated with a catalyst inlet of the axial moving bed reactor (1);

Wherein, the axial moving bed reactor (1) is provided with at least two catalyst beds (3) arranged up and down and optionally a catalyst regeneration bed, the axial moving bed reactor (1) is provided with a feed inlet (2) above each catalyst bed (3);

A catalyst delivery pipe (16) is arranged between two adjacent catalyst beds (3), or if the catalyst regeneration bed is present, between two adjacent beds, so that the catalyst can move from top to bottom in the axial moving bed reactor (I);

Optionally, a separation component (10) is provided between two adjacent catalyst beds (3) and if the catalyst regeneration bed is present as the last bed, between an upstream catalyst bed and the last catalyst regeneration bed, for example, the separation component can be provided in each reaction bed, the inside space of the separation component (10) is communicated with the catalyst delivery pipe (16), the separation component (10) is for separating the stream after the reaction in the upstream catalyst bed from the catalyst, the catalyst obtained by the separation with the separation component (10) moves down through the catalyst delivery pipe (16).

2. The liquid-solid axial moving bed reaction and regeneration apparatus according to technical solution 1, wherein a reaction stream outlet of the last catalyst bed of the axial moving bed reactor (1) is communicated with the feed inlet (2) of the first catalyst bed of the axial moving bed reactor (1) to recycle the reaction stream obtained from the axial moving bed reactor (1) back to the axial moving bed reactor (1).

3. The liquid-solid axial moving bed reaction and regeneration apparatus according to any of technical solutions 1-2, wherein The axial moving bed reactor further comprises at least one catalyst regeneration bed, preferably, the number of the catalyst bed(s) and the number of the catalyst regeneration bed(s) are identical and the catalyst bed and the catalyst regeneration bed are intervally successively arranged, more preferably the number of the catalyst regeneration bed is one less than the number of the catalyst bed, the catalyst bed and the catalyst regeneration bed are intervally successively arranged, and the catalyst reaction beds are arranged both at the top and the bottom of the axial moving bed reactor.

The axial moving bed reactor has a catalyst inlet, which is communicated with the top of the first catalyst bed;

There are a catalyst inlet and a reaction stream inlet at the top of each catalyst bed, the catalyst inlet of the first reaction bed is the catalyst inlet of the axial moving bed reactor, the catalyst inlet of the subsequent reaction bed is communicated with the catalyst delivery pipe;

There are a catalyst outlet communicated with the catalyst delivery conduit and a reaction stream outlet at the bottom of each catalyst bed;

There are a catalyst inlet communicated with the catalyst delivery conduit and a regeneration medium outlet at the top of the catalyst regeneration bed;

There are a catalyst outlet communicated with the catalyst delivery conduit and a regeneration medium inlet at the bottom of the catalyst regeneration bed;

An isolation medium inlet is arranged on the catalyst delivery pipeline for transferring the catalyst from the catalyst regeneration bed to the catalyst bed;

A separation component is arranged at the bottom of each catalyst bed;

Various beds are communicated with each other through the catalyst delivery pipeline;

The bottom of the catalyst bed and the regeneration bed are communicated by means of a catalyst delivery conduit that is inserted into the interior of the regeneration bed, and the outlet of the inserted-type catalyst delivery conduit is below the regeneration medium outlet in the regeneration bed;

The isolation medium inlet and the reaction stream outlet of the last catalyst bed are communicated so that the reaction stream is pressurized with a pump and then used as the isolation medium;

The reaction stream outlet of the upstream catalyst bed is communicated with an inlet for feeding the reaction stream of the downstream catalyst bed, optionally by means of a communication pipeline, and a fresh reaction feedstock inlet can also be arranged on said communication pipeline;

The regeneration medium outlet of an upstream catalyst regeneration bed can be communicated with the regeneration medium inlet of a downstream catalyst regeneration bed by means of a pipeline;

A separation component (10) is provided between two adjacent catalyst beds (3) and if the catalyst regeneration bed is present as the last bed, between an upstream catalyst bed and the last catalyst regeneration bed, for example, the separation component can be provided in each reaction bed, the inside space of the separation component (10) is communicated with the catalyst delivery pipe (16), the separation component (10) is for separating the stream after the reaction in the upstream catalyst bed from the catalyst, the catalyst obtained by the separation with the separation component (10) moves down through the catalyst delivery pipe (16).

4. The liquid-solid axial moving bed reaction and regeneration apparatus according to any of technical solutions 1-3, wherein a reaction stream deflector (11) is provided between two adjacent catalyst beds (3) and if any, between an upstream catalyst bed and the last catalyst regeneration bed, for example, the reaction stream deflector can be provided in each catalyst bed, especially in the bed space of the reaction bed, and the reaction stream deflector (11) is for intensifying the mixing of the stream after the reaction and the liquid-state fresh reaction feedstock fed from the feed inlet (2).

5. The liquid-solid axial moving bed reaction and regeneration apparatus according to technical solution 4, wherein the reaction stream deflector (11) comprises a main axis (11*l*) and a delivering element (112) extending spirally along the axial direction of the main axis.

6. the liquid-solid axial moving bed reaction and regeneration apparatus according to technical solution 4 or 5, wherein the reaction stream deflector (11) comprises a plurality of deflecting plates (113), a plurality of deflecting plates (113) are inclined along the axial direction of the axial moving bed reactor (1), and a plurality of deflecting plates (113) are arranged in a staggered manner with each other to form a flow channel through which the reaction stream can pass.

7. The liquid-solid axial moving bed reaction and regeneration apparatus according to any of technical solutions 1-6, wherein between two adjacent catalyst beds (3) and if a catalyst regeneration bed is present, between two adjacent beds is arranged a catalyst distribution component, which is for dispersing the catalyst at the outlet of the catalyst delivery pipe (16);

Preferably, the catalyst distribution component includes a cone-shaped distribution baffle (12), and the cone-shaped distribution baffle (12) is arranged coaxially with the catalyst delivery pipe (16); further preferably, the number of the cone-shaped distribution baffle (12) is identical to that of the catalyst delivery pipe (16);

Further preferably, the catalyst distribution component further comprises a horizontal distribution baffle (13) arranged below the cone-shaped distribution baffle (12), and the horizontal distribution baffle (13) is provided with holes through which the catalyst can pass.

8. The liquid-solid axial moving bed reaction and regeneration apparatus according to any of technical solutions 1-7, wherein the catalyst regenerator (4) is provided with a fresh catalyst feed inlet for the fresh catalyst to enter the catalyst regenerator (4).

9. The liquid-solid axial moving bed reaction and regeneration apparatus according to any of technical solutions 1-8, wherein a spent catalyst receiver (5), a catalyst regenerator (4) and a regenerated catalyst receiver (6) are successively arranged from top to bottom, and catalyst circulation pipelines for connecting the spent catalyst receiver (5), the catalyst regenerator (4) and the regenerated catalyst receiver (6) are arranged vertically or inclined at an angle relative to the horizontal plane of not less than 40 degrees.

10. The liquid-solid axial moving bed reaction and regeneration apparatus according to any of technical solutions 1-9, wherein on the communication pipeline of the catalyst outlet of the axial moving bed reactor (1) and the catalyst inlet of the spent catalyst receiver (5) is arranged a first particle flow regulator (25); on the communication pipeline of the catalyst outlet of the regenerated catalyst receiver (6) and the catalyst inlet of the axial moving bed reactor (1) is arranged a second particle flow regulator (33);

Preferably, the first particle flow regulator (25) and the second particle flow regulator (33) each independently are an L-shaped or approximately L-shaped stream transportation valve set.

11. The liquid-solid axial moving bed reaction and regeneration apparatus according to any of technical solutions 1-10, wherein the apparatus further comprises a catalyst buffer tank (38), the catalyst buffer tank (38) is arranged between the axial moving bed reactor (1) and the spent catalyst receiver (5), the catalyst inlet of the catalyst buffer tank (38) is communicated with the catalyst outlet of the axial moving bed reactor (1), the catalyst outlet of the catalyst buffer tank (38) is communicated with the catalyst inlet of the spent catalyst receiver (5).

12. A solid acid alkylation process, comprising:

The process is performed in the liquid-solid axial moving bed reaction and regeneration apparatus according to any of technical solutions 1-11, the liquid-phase feedstock is sent into the axial moving bed reactor from the feed inlet above each catalyst bed and contacted with the catalyst to perform the reaction.

13. The process according to technical solution 12, wherein the process further comprises: the reaction product obtained at the bottom of the axial moving bed reactor (1) (i.e. obtained from the reaction stream outlet of the last catalyst bed) is recycled to a position above the uppermost upstream catalyst bed and mixed with the liquid-phase feedstock and then fed into the reactor.

14. The process according to any of technical solutions 12-13, wherein in the axial moving bed reactor, the reaction temperature is 30-100° C., and the pressure is 1-3.4 MPa;

Preferably, the weight hourly space velocity of the stream entering each catalyst bed based on the alkene is 0.05-1 $h^{-1}$;

Preferably, the molar ratio of isoalkane to alkene in the stream entering each catalyst bed is 200-1000:1;

Preferably, the residence time of the catalyst in the axial moving bed reactor is 6-72 h.

15. The process according to any of technical solutions 12-14, wherein the catalyst is a solid acid catalyst, the solid acid catalyst contains a molecule sieve and a heat-resistant inorganic oxide, based on the total amount of the solid acid catalyst, the content of the molecule sieve is 65-95 wt %, the content of the heat-resistant inorganic oxide is 5-35 wt %;

Preferably, the molecule sieve is selected from at least one of FAU structure zeolite, BETA structure zeolite and MFI structure zeolite, the heat-resistant inorganic oxide is alumina and/or silica;

Further preferably, the solid acid catalyst further contains a metal active component, the metal active component is selected from at least one of Fe, Co, Ni, Pd and Pt, based on the total amount of the solid acid catalyst, the content of the metal active component is 0.15-2 wt %.

16. the process according to any of technical solutions 12-15, wherein between two adjacent catalyst beds (3) is provided a separation component (10), for example, the separation component may be arranged in each reaction bed, the inside space of the separation component (10) is communicated with the catalyst delivery pipe (16), the separation component (10) is for separating the stream after the reaction in the upstream catalyst bed from the catalyst, the catalyst obtained by the separation with the separation component (10) moves down through the catalyst delivery pipe (16).

17. The process according to any of technical solutions 12-16, wherein a reaction stream deflector (11) is provided between two adjacent catalyst beds (3), for example, a reaction stream deflector may be arranged in each catalyst bed, especially in the bed space of the reaction bed; and the reaction stream deflector (11) is for intensifying the mixing of the stream after the reaction and the liquid-state fresh reaction feedstock fed from the feed inlet (2);

Preferably, the reaction stream deflector (11) comprises a main axis (111) and a delivering element (112) extending spirally along the axial direction of the main axis;

Preferably, the reaction stream deflector (11) comprises a plurality of deflecting plates (113), a plurality of deflecting plates (113) are inclined along the axial direction of the axial moving bed reactor (1), and a plurality of deflecting plates (113) are arranged in a staggered manner with each other to form a flow channel through which the reaction stream can pass.

18. The process according to any of technical solutions 12-17, wherein between two adjacent catalyst beds (3) is arranged a catalyst distribution component, which is for dispersing the catalyst at the outlet of the catalyst delivery pipe (16);

Preferably, the catalyst distribution component includes a cone-shaped distribution baffle (12), and the cone-shaped distribution baffle (12) is arranged coaxially with the catalyst delivery pipe (16); further preferably, the number of the cone-shaped distribution baffle (12) is identical to that of the catalyst delivery pipe (16);

Further preferably, the catalyst distribution component further comprises a horizontal distribution baffle (13) arranged below the cone-shaped distribution baffle (12), and the horizontal distribution baffle (13) is provided with holes through which the catalyst can pass.

19. The process according to any of technical solutions 12-18, wherein the catalyst at the bottom of the axial moving bed reactor (1) is transported to the spent catalyst receiver (5) to remove the liquid-phase stream carried in the catalyst, and then transported to the catalyst regenerator (4) for regeneration;

Preferably, the superficial flow velocity of the regeneration medium in the catalyst regenerator (4) is 0.003-0.8 m/s, further preferably 0.02-0.5 m/s.

20. the process according to any of technical solutions 12-19, wherein the catalyst regenerator (4) is provided with a fresh catalyst feed inlet for the fresh catalyst to enter the catalyst regenerator (4).

21. The process according to any of technical solutions 12-20, wherein a spent catalyst receiver (5), a catalyst regenerator (4) and a regenerated catalyst receiver (6) are successively arranged from top to bottom, and catalyst circulation pipelines for connecting the spent catalyst receiver (5), the catalyst regenerator (4) and the regenerated catalyst receiver (6) are arranged vertically or inclined at an angle relative to the horizontal plane of not less than 40 degrees.

22. The process according to any of technical solutions 12-21, wherein on the communication pipeline of the catalyst outlet of the axial moving bed reactor (1) and the catalyst inlet of the spent catalyst receiver (5) is arranged a first particle flow regulator (25); on the communication pipeline of the catalyst outlet of the regenerated catalyst receiver (6) and the catalyst inlet of the axial moving bed reactor (1) is arranged a second particle flow regulator (33);

Preferably, the first particle flow regulator (25) and the second particle flow regulator (33) each independently are an L-shaped or approximately L-shaped stream transportation valve set.

23. The process according to any of technical solutions 12-22, wherein the apparatus further comprises a catalyst buffer tank (38), the catalyst buffer tank (38) is arranged between the axial moving bed reactor (1) and the spent catalyst receiver (5), the catalyst inlet of the catalyst buffer tank (38) is communicated with the catalyst outlet of the axial moving bed reactor (1), the catalyst outlet of the catalyst buffer tank (38) is communicated with the catalyst inlet of the spent catalyst receiver (5).

24. The process according to any of technical solutions 12-23, wherein the axial moving bed reactor (1) is provided with a catalyst regeneration bed, which is located below a reaction bed, the catalyst leaving the reaction bed enters the catalyst regeneration bed, and is regenerated in the presence of a liquid hydrocarbon in which hydrogen is dissolved, the regeneration conditions in the catalyst regeneration bed comprise:

The regeneration temperature is 50-140° C.,

The superficial flow velocity of the regeneration medium in the regenerator is 0.01-0.5 m/s;

The regeneration medium is a liquid hydrocarbon in which hydrogen is dissolved; the liquid hydrocarbon is C3-C6 (for example C3-C5) saturated alkane or a mixture of the reaction product and the above-mentioned saturated alkane, preferably, the liquid hydrocarbon is a mixture of C3-C6 (for example C3-C5) saturated alkane and the reaction product.

25. The process according to any of technical solutions 12-24, wherein

The fresh feedstock and the recycled stream or the stream after the reaction in the upstream catalyst bed enter the axial moving bed reactor, and contact with the catalyst on the catalyst bed to perform the reaction; the stream after the reaction enters the next reaction bed or finally leaves the reactor through the separation component, the catalyst that does not pass through the separation component moves down through the catalyst delivery pipe to enter the downstream reaction bed for the reaction or to enter the catalyst regeneration bed for the low temperature regeneration, the catalyst after the low temperature regeneration moves down through the catalyst delivery pipe to enter the downstream reaction bed.

26. The process according to any of technical solutions 12-25, wherein

The intensified mixing of the stream after the reaction passing through the separation component and the fresh feedstock is carried out under the action of the reaction stream deflector;

A catalyst distribution component is arranged between two adjacent beds, the catalyst passing through the catalyst delivery pipe from the upstream bed is dispersed under the action of the catalyst distribution component and falls to the downstream bed;

The lower part of the axial moving bed reactor is provided with a bottom catalyst-collecting area; the catalyst passing through the most downstream catalyst bed is sent to the bottom catalyst-collecting area, and then sent to spent catalyst receiver;

A first particle flow regulator is arranged on the communication pipeline between the catalyst outlet of the axial moving bed reactor and the catalyst inlet of the spent catalyst receiver to adjust the flow of catalyst particles;

An outlet for withdrawing the liquid-phase stream is arranged at the bottom of the spent catalyst receiver, the liquid-phase stream carried in the catalyst is removed in the spent catalyst receiver, a removed liquid filter is arranged on the delivery pipeline for withdrawing the liquid-phase stream starting from the outlet for withdrawing the liquid-phase stream to block fine catalyst powder or fine catalyst particles;

The liquid-withdrawn catalyst in the spent catalyst receiver is sent to the catalyst regenerator for regeneration, and the catalyst regenerator is provided with an inlet for feeding the regeneration medium and an outlet for discharging the regeneration medium;

The regeneration medium is fed into the catalyst regenerator through the inlet for feeding the regeneration medium and contacts with the catalyst to regenerate the catalyst, and the regeneration medium is discharged through an outlet for discharging the regeneration medium;

On the regeneration medium delivery pipeline starting from the outlet for discharging the regeneration medium, is arranged a medium-after-regeneration filter to block the fine powder or the fine particles;

The catalyst regenerator is optionally provided with a fresh catalyst feed inlet for the fresh catalyst to enter the catalyst regenerator;

The regenerated catalyst flows into the regenerated catalyst receiver through the catalyst delivery pipeline at the bottom of the catalyst regenerator, the regenerated catalyst receiver is provided with an inlet for supplementing the liquid-phase stream, and the liquid-phase stream is introduced into the regenerated catalyst receiver through the inlet for supplementing the liquid-phase stream to replace the gas in the gap of the catalyst;

The regenerated catalyst will return to the axial moving bed reactor through the catalyst delivery conduit between the regenerated catalyst receiver and the axial moving bed reactor to continue participating in the reaction until it is deactivated and transported to the spent catalyst receiver;

A second particle flow regulator is provided on the communication pipeline of the catalyst outlet of the regenerated catalyst receiver and the catalyst inlet of the axial moving bed reactor to adjust the flow of catalyst particles.

27. The process according to any of technical solutions 12-26, wherein:

The axial moving bed reactor comprises:

At least one, preferably, at least two catalyst beds (also known as reaction beds) and at least one catalyst regeneration bed, preferably, the reaction bed number is identical to the catalyst regeneration bed number and the reaction bed(s) and the catalyst regeneration bed(s) are intervally successively arranged, more preferably the number of the catalyst regeneration bed is one less than the number of the catalyst bed, the catalyst bed and the catalyst regeneration bed are intervally successively arranged, and the catalyst reaction beds are arranged both at the top and the bottom of the axial moving bed reactor;

The axial moving bed reactor has a catalyst inlet, which is communicated with the top of the first reaction bed;

There are a catalyst inlet and an inlet for feeding the reaction stream at the top of each reaction bed, the catalyst inlet of the first reaction bed is the catalyst inlet of the axial moving bed reactor, and the catalyst inlet of the subsequent reaction bed is communicated with the catalyst delivery pipe;

There are a catalyst outlet communicated with the catalyst delivery conduit and a reaction stream outlet at the bottom of each reaction bed;

There are a catalyst inlet communicated with the catalyst delivery conduit and a regeneration medium outlet at the top of the catalyst regeneration bed;

There are a catalyst outlet communicated with the catalyst delivery conduit and a regeneration medium inlet at the bottom of the catalyst regeneration bed;

An isolation medium inlet is arranged on the catalyst delivery pipeline for transferring the catalyst from the catalyst regeneration bed to the catalyst bed;

A separation component is provided at the bottom of each reaction bed;

Various beds are communicated with each other through the catalyst delivery pipeline;

The bottom of the catalyst bed and the regeneration bed are communicated by means of a catalyst delivery conduit that is inserted into the interior of the regeneration bed, the outlet of the inserted-type catalyst delivery conduit is below the regeneration medium outlet in the regeneration bed;

The isolation medium is preferably a recycled stream pressurized by a pump after the reaction, and the isolation medium inlet is communicated with the reaction stream outlet of the last reaction bed;

The stream after the reaction passes through the separation component to enter the next reaction bed or be finally discharged, and the catalyst that does not pass through the separation component moves down through the catalyst delivery pipe;

The reaction stream outlet of the upstream reaction bed is communicated with the inlet for feeding the reaction stream of the downstream reaction bed, optionally through a communication pipeline, and here the communication pipeline is also provided with a fresh reaction feedstock inlet;

The top of the bed refers to being located at 70% or higher of each bed from bottom to top, and the bottom of the bed refers to being located at 20% or lower of each bed from bottom to top;

The regeneration medium outlet of an upstream catalyst regeneration bed can be communicated with the regeneration medium inlet of a downstream catalyst regeneration bed by means of a pipeline;

The inlet for feeding the reaction stream of the reaction bed, the regeneration medium inlet of the catalyst regeneration bed, and the isolation medium inlet arranged on the catalyst delivery pipeline for transferring the catalyst from the catalyst regeneration bed to the catalyst bed are provided with the corresponding stream distributor;

The fresh reaction feedstock and the recycled stream or the stream after the reaction in the upstream the reaction bed enter the reaction bed of the axial moving bed; In the reaction bed, after the distribution with the reaction stream distributor, the mixed stream passes through the reaction bed along the axial direction of the reaction bed, contacts with the solid acid catalyst to perform the reaction, after the completion of the reaction, the majority of the liquid-phase stream leaves this bed through the arranged reaction stream outlet, while the minority of the remaining liquid-phase stream, together with the catalyst particles, enters the next reaction bed or enters the catalyst regeneration bed through the inserted-type conduit between the reaction bed and the catalyst regeneration bed;

The discharged liquid-phase stream after the reaction enters the next reaction bed together with the fresh reaction feedstock to continue to participate in the reaction or directly leaves the reaction bed, and the alkylation oil product is collected after the separation (e.g., distillation);

In the catalyst regeneration bed, the catalyst contacts in countercurrent with a liquid-phase regeneration medium in which hydrogen is dissolved under the regeneration condition (low temperature regeneration), so that unsaturated hydrocarbons adsorbed on the catalyst are converted into saturated hydrocarbon molecules which are easy to desorb and are taken out of the catalyst regeneration bed to realize the partial regeneration of the catalyst;

The regenerated catalyst will flow into the next reaction bed through the catalyst delivery pipeline at the bottom of the catalyst regeneration bed;

During the course of transporting the catalyst from the bottom of the catalyst regeneration bed to the reaction bed, the isolation medium enters through the isolation medium inlet arranged on the delivery pipeline and replaces the liquid-phase medium that is descending together with the catalyst;

The inactivation degree of the catalyst in each bed of the moving bed gradually increases along with the reaction and the increased regeneration number, and meanwhile the catalyst also gradually falls to the lower bed and finally reaches the bottom of the moving bed reactor; Finally, the catalyst is sent to the catalyst regenerator for high-temperature deep regeneration to realize the complete recovery of the catalyst activity; The catalyst with the recovered activity is sent to the first reaction bed of the moving bed reactor to continuously participate in the reaction, and the process is circulated in this manner;

The reaction conditions in the reaction bed may include:
The reaction temperature is 30-100° C.,
The reaction pressure is 1.0-3.4 MPa, gauge pressure, The superficial flow velocity of the liquid-phase stream in the reactor is 0.03-1 m/s;

The weight hourly space velocity of the mixed alkene feedstock is 0.05-1 h$^{-1}$;

The mole ratio of alkane to alkene at the reaction bed inlet is 200-1000:1;

The average particle diameter of the solid acid catalyst particles is 0.3-3 mm.

The regeneration conditions in the catalyst regeneration bed can comprise:

The regeneration temperature is 50-140° C.,

The superficial flow velocity of the regeneration medium in the regenerator is 0.01-0.5 m/s;

The regeneration medium is a liquid hydrocarbon in which hydrogen is dissolved; the liquid hydrocarbon is C3-C6 (for example C3-C5) saturated alkane or a mixture of the reaction product and the above-mentioned saturated alkane, preferably, the liquid hydrocarbon is a mixture of C3-C6 (for example C3-C5) saturated alkane and the reaction product;

The regeneration conditions in the catalyst regenerator (high temperature deep regeneration) may include:

The regeneration temperature is 180-400° C.,

The regeneration pressure is 0.5-4.0 MPa,

The regeneration medium is hydrogen gas or a mixture of hydrogen gas and low carbon hydrocarbon (for example C3-C8), preferably a mixture of hydrogen gas and low carbon hydrocarbon (for example C3-C8);

The main active component of the catalyst is a molecule sieve loaded with a certain amount of metal, the molecule sieve is one of or a combination of two or more of FAU structure zeolite, BETA structure zeolite, MFI structure zeolite, preferably a zeolite having FAU structure and a zeolite having BETA structure, the metal loaded on the catalyst is one of or a combination of two or more of Fe, Co, Ni, Pd and/or Pt, preferably one of or a combination of two or more of Co, Ni or Pt.

The liquid-solid axial moving bed reaction and regeneration apparatus provided by the present invention has the following advantages:

1) Compared with the fixed-bed alkylation technology, only one reactor is needed to realize the continuous and stable operation of the reaction apparatus;

2) Compared with the fluidized bed alkylation technology, the liquid-solid axial moving bed reaction and regeneration apparatus provided by the present invention can realize the life distribution of the catalyst, and can remove a part of the deactivated catalyst from the system, and then supplement the fresh catalyst; while the fluidized bed reactor cannot achieve the life distribution of the catalyst;

3) In the liquid-solid axial moving bed reaction and regeneration apparatus provided by the present invention, the axial moving bed reactor is used. A single set of equipment can meet the requirements, and the investment cost of the apparatus is reduced. In addition, the inactivated catalyst particles are led out of the reactor for deep regeneration, the continuous operation of the reaction and regeneration of the catalyst is realized on the premise of not influencing the stable operation of the reaction apparatus, the relatively stable equilibrium activity of the catalyst in the apparatus is maintained, and the selectivity of the target product in the alkylation oil is improved.

The solid acid alkylation process provided by the present invention has the following advantages:

1) Compared with the fixed-bed alkylation technology, only one reactor is needed to realize the continuous and stable operation of the reaction apparatus;

2) Compared with the fluidized bed alkylation technology, the process provided by the present invention can realize the life distribution of the catalyst, and can remove a part of the deactivated catalyst from the system, and then supplement the fresh catalyst; while the fluidized bed reactor cannot achieve the life distribution of the catalyst;

3) The process provided by the present invention uses the axial moving bed reactor. A single set of equipment can meet the requirements, and the investment cost of the apparatus is reduced. In addition, the inactivated catalyst particles are led out of the reactor for deep regeneration, the continuous operation of the reaction and regeneration of the catalyst is realized on the premise of not influencing the stable operation of the reaction apparatus, the relatively stable equilibrium activity of the catalyst in the apparatus is maintained, and the selectivity of the target product in the alkylation oil is improved.

DESCRIPTION OF THE REFERENCE NUMERALS

Figure 1:
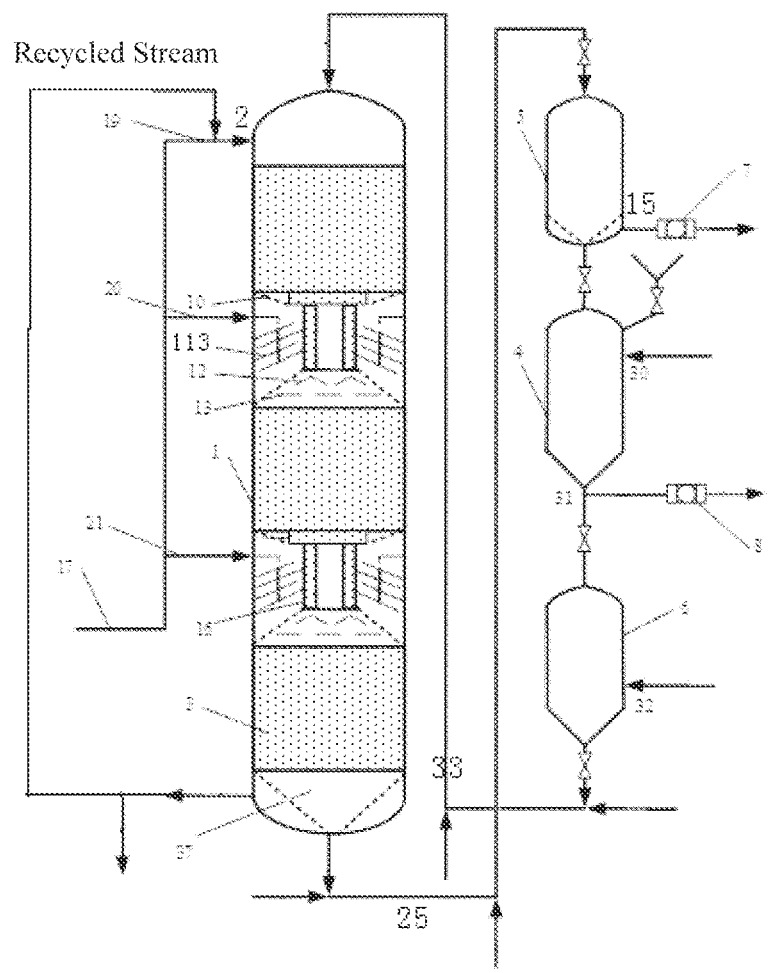
FIG. 1 shows a liquid-solid axial moving bed reaction and regeneration apparatus according to a specific embodiment provided by the present invention.

1: Axial moving bed reactor
2: Feed inlet
3: Catalyst bed
4: catalyst regenerator
5: Spent catalyst receiver
6: Regenerated catalyst receiver
7: Removed liquid filter
8: Medium-after-regeneration filter
10: Separation component
11: Reaction stream deflector
111: Main axis
112: Delivering element
113: Deflecting plate
12: Cone-shaped distribution baffle
13: Horizontal distribution baffle
15: Outlet for withdrawing the liquid-phase stream
16: Catalyst delivery pipe
17: Pipeline
19: First branch pipeline
20: Second branch pipeline
21: Third branch pipeline
25: First particle flow regulator
30: Inlet for feeding the regeneration medium
31: Outlet for discharging the regeneration medium
32: Inlet for supplementing the liquid-phase stream
33: Second particle flow regulator
37: Bottom catalyst-collecting area
38: Catalyst buffer tank
51, 53: Reaction beds
52, 54: Catalyst regeneration beds
55: Fresh reaction feedstock
56, 57: Fresh reaction feedstock inlet 58: Recycled stream
59, 61: Reaction stream outlets
60: Inlet for feeding the reaction stream
62: Catalyst inlet
63, 64, 65, 66: Catalyst delivery conduits
67, 69: Regeneration medium inlets
68, 71: Regeneration medium outlets
70: Isolation medium inlet
72: Separation component

DETAILED DESCRIPTION OF THE INVENTION

The end points of the ranges and any values disclosed herein are not limited to the precise ranges or values, and these ranges or values should be understood to include the values close to these ranges or values. For numerical ranges, the endpoints of the ranges to each other, the endpoints of the ranges and the individual point values, and the individual point values to each other can be combined with each other to give one or more new numerical ranges, and these new numerical ranges should be construed as specifically disclosed herein.

In the present invention, if no explanation is made to the contrary, the directional words used such as "above", "up", "below", and "down" usually refer to "above", "up", "below", and "down" as shown with reference to the drawings. The orientation words used such as "in", "inside", "out" and "outside" refer to the inner and outer part relative to the contour of each component itself.

In the present invention, "above the bed", "the top of the bed", or the like refers to being located at 70% or higher of each bed from bottom to top, and "the bottom of the bed", or the like refers to being located at 20% or lower of each bed from bottom to top.

In one aspect, the present invention provides a liquid-solid axial moving bed reaction and regeneration apparatus, the apparatus comprises:

An axial moving bed reactor 1, a spent catalyst receiver 5, a catalyst regenerator 4 and a regenerated catalyst receiver 6 are successively connected, wherein the catalyst outlet of the regenerated catalyst receiver 6 is communicated with the catalyst inlet of the axial moving bed reactor 1;

Wherein, the axial moving bed reactor 1 is provided with at least two catalyst beds 3 arranged up and down, the axial moving bed reactor 1 is provided with a feed inlet 2 above each catalyst bed 3;

A catalyst delivery pipe 16 is arranged between two adjacent catalyst beds 3 so that the catalyst can move from top to bottom in the axial moving bed reactor 1;

In the present invention, the expression "successively connected" means that the catalyst outlet of the axial moving bed reactor 1 is connected to the catalyst inlet of the spent catalyst receiver 5, the catalyst outlet of the spent catalyst receiver 5 is connected to the catalyst inlet of the catalyst regenerator 4, the catalyst outlet of the catalyst regenerator 4 is connected to the catalyst inlet of the regenerated catalyst receiver 6. The catalyst outlet of the regenerated catalyst receiver 6 is communicated with the catalyst inlet of the axial moving bed reactor 1 to send the regenerated catalyst into the axial moving bed reactor 1.

The axial moving bed reactor of the present invention refers to a moving bed reactor in which the moving direction of the catalyst is in the axial direction.

According to the apparatus provided by the present invention, the axial moving bed reactor 1 is provided with at least two catalyst beds 3 arranged up and down, preferably 3-8 catalyst beds 3 arranged up and down. The present invention has no particular limitation on the thickness of the catalyst bed 3. Preferably, the thickness of each catalyst bed 3 is each independently 10-30% of the height of the axial moving bed reactor 1.

In the examples of the present invention, an axial moving bed reactor 1 having a height of 7.5 m and an inner diameter of 600 mm is taken as an example to illustrate the present invention, but the present invention is not limited thereto. Those skilled in the art can make appropriate adjustments according to the practical situation. In an embodiment, the axial moving bed reactor 1 has a height of 5-75 meters and an inner diameter of 200-3000 mm.

According to the apparatus provided by the present invention, the axial moving bed reactor 1 is provided with a feed inlet 2 above each catalyst bed 3. The liquid-state fresh reaction feedstock is sent into the axial moving bed reactor 1 from the feed inlet 2 of the axial moving bed reactor 1 and contacted with the catalyst filled in the catalyst bed 3 to perform the reaction. The catalyst in the uppermost catalyst bed 3 of the axial moving bed reactor 1 is contacted with the liquid-state fresh reaction feedstock to perform the reaction; and the catalyst in other catalyst beds 3 is contacted with a mixture of the liquid-state fresh reaction feedstock and the stream after the reaction coming from the upstream catalyst bed 3 to perform the reaction. With the apparatus provided by the present invention, the liquid-state fresh reaction feedstock can be fed into the axial moving bed reactor 1 through different feed inlets 2, which is more conducive to controlling the temperature rise.

According to the present invention, the catalyst delivery pipe 16 is not particularly limited, so long as it can achieve the catalyst is capable of moving in the axial moving bed reactor 1 from top to bottom. Specifically, the catalyst delivery pipe may be cylindrical. One catalyst delivery pipe 16 can be arranged between two adjacent catalyst beds 3, or two or more catalyst delivery pipes 16 can be arranged between two adjacent catalyst beds 3. The inner diameter and the number of the catalyst delivery pipe 16 are appropriately selected according to the inner diameter of the axial moving bed reactor 1. For example, relative to the axial moving bed reactor 1 having an inner diameter of 600 mm, 2-5 catalyst delivery pipes 16 can be arranged between two adjacent catalyst beds 3, and the inner diameter of the catalyst delivery pipe 16 can be 15-50 mm. In an embodiment, the axial moving bed reactor 1 has a height of 5-75 meters and an inner diameter of 200-3000 mm, 2-5 catalyst delivery pipes 16 can be arranged between two adjacent catalyst beds 3, and the inner diameter of the catalyst delivery pipe 16 can be 5-150 mm.

According to a preferred embodiment of the present invention, the reaction stream outlet of the axial moving bed reactor 1 (preferably arranged at the bottom) is communicated with the uppermost feed inlet 2 of the axial moving bed reactor 1 to recycle the reaction stream obtained from the axial moving bed reactor 1 back to the axial moving bed reactor 1. With this preferred embodiment, it is more conducive to control the alkane/alkene ratio of each catalyst bed 3, and is more conducive to control the temperature rise of the catalyst bed 3.

In the present invention, the catalyst bed is also called the reaction bed, two adjacent catalyst beds means an upstream reaction bed and a downstream reaction bed thereof; If the catalyst regeneration bed is not included, two adjacent catalyst beds means two upstream and downstream catalyst beds, While if a catalyst regeneration bed that is not the last bed is included, two adjacent catalyst beds means a catalyst bed (namely the reaction bed) that is the first bed upstream the catalyst regeneration bed but not a catalyst regeneration bed, and a catalyst bed (namely the reaction bed) that is the first bed downstream the catalyst regeneration bed but not a catalyst regeneration bed respectively.

In the present invention, between two adjacent beds means between any two adjacent beds, comprising: between an upstream catalyst bed (namely the reaction bed) and a downstream catalyst bed (namely the reaction bed), between an upstream catalyst bed (namely the reaction bed) and a downstream catalyst regeneration bed, between an upstream catalyst regeneration bed and a downstream catalyst bed (namely the reaction bed), between an upstream catalyst regeneration bed and a downstream catalyst regeneration bed.

According to a preferred embodiment of the present invention, a separation component 10 is arranged between two adjacent catalyst beds 3 and if any, between the upstream catalyst bed (reaction bed) and the last catalyst regeneration bed (for example, a separation component 10 may be arranged in each reaction bed), the inside space of the separation component 10 is communicated with the catalyst delivery pipe 16, the separation component 10 is for separating the stream after the reaction in the upstream catalyst bed from the catalyst, the catalyst obtained by the separation with the separation component 10 moves down through the catalyst delivery pipe 16. The stream after the reaction in the upstream catalyst bed and the catalyst are separated with the separation component 10 to give the stream after the reaction and the catalyst, the catalyst moves down through the catalyst delivery pipe 16, while the stream after the reaction is mixed with a liquid-state fresh reaction feedstock that is introduced through the feed inlet above the catalyst bed 3 in the space between two adjacent catalyst beds (in the present invention, it is called the bed space before the reaction bed), and then the resulting mixture flows into the downstream catalyst bed.

According to a specific embodiment of the present invention, the separation component 10 may be a screen mesh with holes (the hole diameter may be determined according to the size of the catalyst particles), which allows the stream after the reaction to pass through, so as to realize the separation of the stream after the reaction and the catalyst.

In order to achieve a more uniform mixing of the stream after the reaction and the liquid-state fresh reaction feedstock that flow into the downstream catalyst bed, preferably, a reaction stream deflector 11 is arranged between two adjacent catalyst beds 3, the reaction stream deflector 11 is for intensifying the mixing of the stream after the reaction and the liquid-state fresh reaction feedstock fed through the feed inlets 2. For example, a reaction stream deflector may be arranged in each catalyst bed, especially in the bed space of the reaction bed.

In the present invention, the specific structure of the reaction stream deflector 11 is not particularly limited, as long as it can intensify the mixing of the stream after the reaction and the liquid-state fresh reaction feedstock. Specifically, the reaction stream deflector 11 is placed in the bed space before the reaction bed, and its number can be one or two or more, preferably 1-6.

Figure 2:
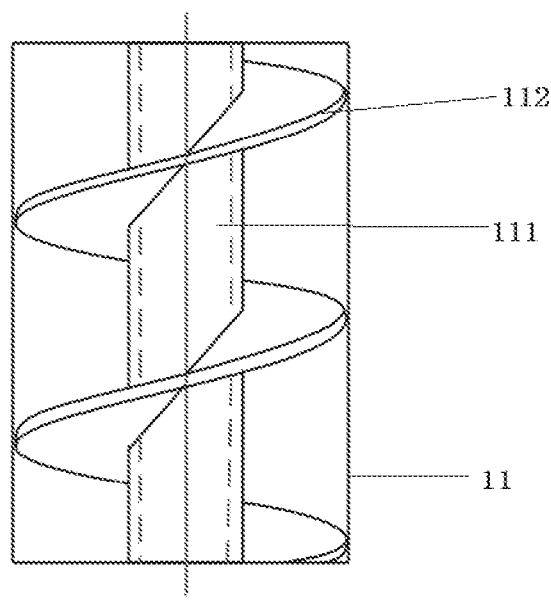
FIG. 2 is a schematic view of a deflector provided by the present invention.

According to the first preferred embodiment of the present invention, as shown in FIG. 2, the reaction stream deflector 11 includes a main axis 111 and a delivering element 112 extending spirally along the axial direction of the main axis. Specifically, the inlet of the spirally extending flow channel formed by the delivering element 112 is set according to the position of the feed inlet 2 so that the stream after the reaction and the liquid-state fresh reaction feedstock flow along the spirally extending flow channel formed by the delivering element 112 to achieve the mixing.

According to the second preferred embodiment of the present invention, as shown in FIG. 1, the reaction stream deflector 11 comprises a plurality of deflecting plates 113, a plurality of deflecting plates 113 are inclined along the axial direction of the axial moving bed reactor 1, and a plurality of deflecting plates 113 are arranged in a staggered manner with each other to form a flow channel through which the reaction stream can pass. A plurality of the deflecting plates 113 can be inclined downwards or upwards along the axial direction of the axial moving bed reactor 1 (as shown in FIG. 1). Preferably, the angle between the extension direction of the deflecting plate 113 and the horizontal plane is 5-60 degrees, further preferably 10-40 degrees.

The deflecting plates 113 arranged in a staggered manner with each other as mentioned in the present invention means the deflecting plates 113 do not form a closed area in relation to each other, so that the reaction stream can flow downward smoothly. According to a specific embodiment of the present invention, as shown in FIG. 1, a part of the deflecting plates 113 are fixedly connected to the wall of the axial moving bed reactor 1, and a part of the deflecting plate 113 are fixedly connected to the wall of the catalyst delivery pipe 16, and the deflecting plates 113 are arranged parallel to each other. Preferably, the distance between the deflecting plates 113 is 15-60 mm.

According to a preferred embodiment of the present invention, between two adjacent catalyst beds 3 and if a catalyst regeneration bed is present, between two adjacent beds, is arranged a catalyst distribution component, which is for dispersing the catalyst at the outlet of the catalyst delivery pipe 16. If no catalyst distribution component is arranged, the catalyst at the outlet of the catalyst delivery pipe 16 is likely to form a cone-shaped accumulation on the downstream catalyst bed. Preferably, the catalyst distribution component comprises a cone-shaped distribution baffle 12, and the cone-shaped distribution baffle 12 is arranged coaxially with the catalyst delivery pipe 16. The catalyst at the outlet of the catalyst delivery pipe 16 falls on the tip of the cone-shaped distribution baffle 12 by gravity, and is dispersed to the horizontal sides of the catalyst delivery pipe 16 under the dispersion action of the cone-shaped distribution baffle 12. Further preferably, the number of the cone-shaped distribution baffle 12 is identical to the number of the catalyst delivery pipe 16.

According to a preferred embodiment of the present invention, the catalyst distribution component further comprises a horizontal distribution baffle 13 arranged below the cone-shaped distribution baffle 12, and the horizontal distribution baffle 13 is provided with holes through which the catalyst can pass. The number of the horizontal distribution baffle 13 is not particularly limited by the present invention, and can be one or two or more, and preferably the horizontal distribution baffle 13 is each arranged in the radial middle position of (and in the axial direction, below) two adjacent cone-shaped distribution baffles 12. The radial direction and the axial direction refers to the radial direction and the axial direction of the axial moving bed reactor 1.

Further preferably, in the horizontally outward direction from the center of the axial moving bed reactor 1, the holes of the horizontal distribution baffle 13 gradually become larger. With this preferred embodiment, a part of the catalyst that is close to the center position of the axial moving bed reactor 1 and dispersed by means of the cone-shaped distribution baffle 12 is passed through the holes of the horizontal distribution baffle 13, and another part of the catalyst that cannot pass through is dispersed to the edge position of the axial moving bed reactor 1, which is more conducive to ensuring the uniform dispersion of the catalyst.

Further preferably, the horizontal distribution baffle 13 may be a circular distribution plate with a low opening rate in the center area and a high opening rate at the edge wall.

The catalyst in each catalyst bed of the axial moving bed reactor 1 gradually deactivates and gradually falls to a further downstream catalyst bed (reaction bed) or catalyst regeneration bed along with the reaction, finally reaches the bottom of the axial moving bed reactor 1, and then is transported to the spent catalyst receiver 5 through the catalyst delivery pipeline.

According to a preferred embodiment of the present invention, a bottom catalyst-collecting area 37 is provided at the lower part of the axial moving bed reactor 1. The catalyst passing through the most downstream catalyst bed is sent to the bottom catalyst-collecting area 37, and a certain amount of the catalyst is collected and sent to the spent catalyst receiver 5.

According to a specific embodiment of the present invention, as shown in FIG. 1, the stream pipeline valves between the containers are arranged respectively on the communication pipelines of the axial moving bed reactor 1 and the spent catalyst receiver 5, the spent catalyst receiver 5 and the catalyst regenerator 4, the catalyst regenerator 4 and the regenerated catalyst receiver 6, and the regenerated catalyst receiver 6 and the axial moving bed reactor 1.

According to a preferred embodiment of the present invention, the spent catalyst receiver 5 (preferably the bottom) is provided with an outlet for withdrawing the liquid-phase stream 15. According to the present invention, the liquid-phase stream carried in the catalyst can be removed by means of directly reducing the pressure or increasing the pressure by introducing high-pressure hydrogen, nitrogen and the like in the spent catalyst receiver 5, and the liquid-phase stream can be discharged through the outlet for withdrawing the liquid-phase stream 15. Preferably, a removed liquid filter 7 is arranged on a delivery pipeline for withdrawing the liquid-phase stream starting from the outlet for withdrawing the liquid-phase stream 15. The removed liquid filter 7 is used to block fine catalyst powder or fine catalyst particles.

The liquid-withdrawn catalyst in the spent catalyst receiver 5 is sent to the catalyst regenerator 4 for regeneration. The catalyst regenerator 4 is provided with an inlet for feeding the regeneration medium 30 and an outlet for discharging the regeneration medium 31. The regeneration medium is introduced into the catalyst regenerator 4 through the inlet for feeding the regeneration medium 30 and contacted with the catalyst for the regeneration of the catalyst (preferably full regeneration), and the regeneration medium is discharged through the outlet for discharging the regeneration medium 31. Preferably, a medium-after-regeneration filter 8 is arranged on a regeneration medium delivery pipeline starting from the outlet for discharging the regeneration medium 31. The filter is used to block the catalyst of the regenerator from flowing into the downstream gas circulation pressurizing equipment and to collect the fine powder or fine particles generated during the regeneration process due to friction or purging.

The regeneration medium of the present invention can be air or a mixture of air and nitrogen.

According to a preferred embodiment of the present invention, the catalyst regenerator 4 may also be provided with a fresh catalyst feed inlet for the fresh catalyst to enter the catalyst regenerator 4. By providing the catalyst regenerator 4 with the fresh catalyst feed inlet, a part of the catalyst that has lost its activity or the catalyst that is difficult to restore the initial activity can be replaced with a fresh catalyst to ensure the processing capacity of the apparatus. Specifically, a pump is provided on the fresh catalyst delivery pipeline communicating with the fresh catalyst feed inlet.

The regenerated catalyst will flow into the regenerated catalyst receiver 6 through the catalyst delivery pipeline at the bottom of the catalyst regenerator 4.

Preferably, the regenerated catalyst receiver 6 is provided with an inlet for supplementing the liquid-phase stream 32. With introducing the alkane in the reaction feedstock or the liquid-phase stream after the reaction to the regenerated catalyst receiver 6 through the inlet for supplementing the liquid-phase stream 32, the liquid-phase stream replaces the gas in the gap of the catalyst.

The regenerated catalyst will return to the axial moving bed reactor 1 through the catalyst delivery conduit between the regenerated catalyst receiver 6 and the axial moving bed reactor 1, and continue to participate in the reaction until it is deactivated and transported to the spent catalyst receiver 5. The catalyst is circulated according to the above protocol.

According to a preferred embodiment of the present invention, the spent catalyst receiver 5, the catalyst regenerator 4 and the regenerated catalyst receiver 6 are successively arranged from top to bottom, catalyst circulation pipelines for connecting the spent catalyst receiver 5, the catalyst regenerator 4 and the regenerated catalyst receiver 6 are arranged vertically or inclined at an angle relative to the horizontal plane of not less than 40 degrees. Using this preferred embodiment is more convenient for the smooth flow of the stream of catalyst particles from top to bottom, and prevents the stream from accumulating or remaining in the pipeline, which affects the valve sealing performance or the catalyst regeneration effect.

According to a preferred embodiment of the present invention, on the communication pipeline of the catalyst outlet of the axial moving bed reactor 1 and the catalyst inlet of the spent catalyst receiver 5 is arranged a first particle flow regulator 25; and on the communication pipeline of the catalyst outlet of the regenerated catalyst receiver 6 and the catalyst inlet of the axial moving bed reactor 1 is arranged a second particle flow regulator 33. The first particle flow regulator 25 and the second particle flow regulator 33 is not particularly limited by the present invention, as long as the flow rate of the catalyst particles can be adjusted. Further preferably, the first particle flow regulator 25 and the second particle flow regulator 33 each independently are L-shaped or approximately L-shaped stream transportation valve set. Specifically, the L-shaped or approximately L-shaped stream transportation valve set is also communicated with at least one liquid-phase stream feeding pipeline. Arranging the particle flow regulator can increase the flow resistance of the particle stream. At the same time, the regulator is communicated with at least one liquid-phase stream feeding pipeline to increase the flow driving force of the particle stream and reduce the flow resistance of the particle stream. By arranging L-shaped or approximately L-shaped stream transportation valve set and by changing the flow of the liquid-phase stream entering the valve set, the discharge rate of the catalyst can be adjusted, so that the falling rate and the residence time in each reaction bed of the catalyst in the reactor can be controlled and adjusted.

According to a preferred embodiment of the present invention, the apparatus further comprises a catalyst buffer tank 38, the catalyst buffer tank 38 is arranged between the axial moving bed reactor 1 and the spent catalyst receiver 5, the catalyst inlet of the catalyst buffer tank 38 is communicated with the catalyst outlet of the axial moving bed reactor 1, and the catalyst outlet of the catalyst buffer tank 38 is communicated with the catalyst inlet of the spent catalyst receiver 5. The catalyst buffer tank 38 is used for storing the catalyst discharged from the axial moving bed reactor 1 during the periods of withdrawing the liquid-phase stream from the spent catalyst receiver and discharging the catalyst to the catalyst regenerator, ensuring the flow continuity of the catalyst stream in the axial moving bed reactor 1 and the smoothness of the apparatus operation.

In an embodiment of the present invention, the axial moving bed reactor comprises:

At least one, preferably, at least two catalyst beds (also known as reaction beds) and at least one catalyst regeneration bed, preferably, the reaction bed number is identical to the catalyst regeneration bed number and the reaction beds 51, 53 and the catalyst regeneration beds 52, 54 are intervally successively arranged, more preferably the number of the catalyst regeneration bed is one less than the number of the catalyst bed, the catalyst bed and the catalyst regeneration bed are intervally successively arranged, and the catalyst reaction beds are arranged both at the top and the bottom of the axial moving bed reactor;

The axial moving bed reactor has a catalyst inlet 62, which is communicated with the top of the first reaction bed;

There are a catalyst inlet and an inlet for feeding the reaction stream 60 at the top of each reaction bed, the catalyst inlet of the first reaction bed is the catalyst inlet of the axial moving bed reactor, and the catalyst inlet of the subsequent reaction bed is communicated with the catalyst delivery pipe;

There are the catalyst outlets communicated with the catalyst delivery conduits 63, 65 and the reaction stream outlets 59, 61 at the bottom of each reaction bed.

There are the catalyst inlets communicated with the catalyst delivery conduits 63, 65 and the regenerating medium outlets 68, 71 at the top of the catalyst regeneration bed;

There are the catalyst outlets communicated with the catalyst delivery conduit 64, 66 and the regenerating medium outlets 67, 69 at the bottom of the catalyst regeneration bed;

An isolation medium inlet 70 is arranged on the catalyst delivery pipeline for transferring the catalyst from the catalyst regeneration bed to the catalyst bed;

A separation component 72 is arranged at the bottom of each reaction bed;

Various beds are communicated with each other through the catalyst delivery pipeline;

The bottom of the catalyst bed and the regeneration bed are communicated by means of a catalyst delivery conduit that is inserted into the interior of the regeneration bed, the outlet of the inserted-type catalyst delivery conduit is below the regeneration medium outlet in the regeneration bed;

The isolation medium is preferably a recycled stream pressurized by a pump after the reaction. Therefore, the isolation medium inlet 70 is communicated with the reaction stream outlet 61 of the last reaction bed;

The stream after the reaction passes through the separation component 72 to enter the next reaction bed or be finally discharged, and the catalyst that does not pass through the separation component 72 moves down through the catalyst delivery pipe;

The reaction stream outlet 59 of the upstream reaction bed is communicated with the inlet for feeding the reaction stream 60 of the downstream reaction bed through a pipeline, and the communication pipeline is also provided with fresh reaction feedstock inlet(s) 56, 57;

The top of the bed refers to being located at 70% or higher of each bed from bottom to top, and the bottom of the bed refers to being located at 20% or lower of each bed from bottom to top;

The regeneration medium outlet 68 of the upstream catalyst regeneration bed is communicated with the regeneration medium inlet 69 of the downstream catalyst regeneration bed through a pipeline;

The inlet for feeding the reaction stream 60 of the reaction bed, the regeneration medium inlet of the catalyst regeneration bed, and the isolation medium inlet 70 arranged on the catalyst delivery pipeline for transferring the catalyst from the catalyst regeneration bed to the catalyst bed are provided with the corresponding stream distributor.

With the liquid-solid axial moving bed reaction and regeneration apparatus provided by the present invention, the continuous and stable operation of the solid acid alkylation reaction and the deactivated catalyst regeneration can be realized, the selectivity of the target product and the flexibility of the apparatus operation are improved, the catalyst investment cost is greatly reduced, and the economic competitiveness of the apparatus is increased.

Accordingly, the present invention also provides use of the above-mentioned liquid-solid axial moving bed reaction and regeneration apparatus in the solid acid alkylation reaction.

In another aspect, the present invention provides a solid acid alkylation process, wherein: the process is performed in a liquid-solid axial moving bed reaction and regeneration apparatus, the liquid-solid axial moving bed reaction and regeneration apparatus comprises:

An axial moving bed reactor 1, a spent catalyst receiver 5, a catalyst regenerator 4 and a regenerated catalyst receiver 6 are successively connected, wherein the catalyst outlet of the regenerated catalyst receiver 6 is communicated with the catalyst inlet of the axial moving bed reactor 1;

The axial moving bed reactor 1 is provided with at least two catalyst beds 3 arranged up and down, the axial moving bed reactor 1 is provided with a feed inlet 2 above each catalyst bed 3;

A catalyst delivery pipe 16 is arranged between two adjacent catalyst beds 3 so that the catalyst can move from top to bottom in the axial moving bed reactor 1;

The liquid-phase feedstock is sent into the axial moving bed reactor 1 from the feed inlet above each catalyst bed 3 and contacted with the catalyst to perform the reaction.

In the present invention, the expression "successively connected" means that the catalyst outlet of the axial moving bed reactor 1 is connected to the catalyst inlet of the spent catalyst receiver 5, the catalyst outlet of the spent catalyst receiver 5 is connected to the catalyst inlet of the catalyst regenerator 4, the catalyst outlet of the catalyst regenerator 4 is connected to the catalyst inlet of the regenerated catalyst receiver 6. The catalyst outlet of the regenerated catalyst receiver 6 is communicated with the catalyst inlet of the axial moving bed reactor 1 to send the regenerated catalyst into the axial moving bed reactor 1.

The axial moving bed reactor of the present invention refers to a moving bed reactor in which the moving direction of the catalyst is in the axial direction.

According to the process provided by the present invention, the axial moving bed reactor 1 is provided with at least two catalyst beds 3 arranged up and down, preferably 3-8 catalyst beds 3 arranged up and down. The present invention has no particular limitation on the thickness of the catalyst bed 3. Preferably, the thickness of each catalyst bed 3 is each independently 10-30% of the height of the axial moving bed reactor 1.

In the examples of the present invention, an axial moving bed reactor 1 having a height of 7.5 m and an inner diameter of 600 mm is taken as an example to illustrate the present invention, but the present invention is not limited thereto. Those skilled in the art can make appropriate adjustments according to the practical situation. In an embodiment, the axial moving bed reactor 1 has a height of 5-75 meters and an inner diameter of 200-3000 mm.

The liquid-phase feedstock according to the present invention can be any of various feedstocks conventionally used in the art capable of performing the solid acid alkylation reactions. For example, the liquid-phase feedstock contains isoalkanes and alkenes. The isoalkane may be an isoalkane commonly used in the alkylation reaction, preferably C4-C6 isoalkane, and more preferably isobutane. The alkene is preferably mono-alkene, more preferably C3-C6 mono-alkene, and further preferably C4 mono-alkene. The alkylation feedstock is a hydrocarbon fraction containing alkene and alkane, preferably C4 fraction containing C4 alkene and C4 alkane, more preferably a mixture of C4 alkene and C4 alkane. In one embodiment, the alkane fraction further comprises a light hydrocarbon fraction that passes through the top of the fractionation column, is cooled and returns back to the reactor inlet. In an embodiment, the alkylation feedstock is a hydrocarbon fraction containing alkene and alkane, wherein the mole ratio of alkane to alkene is 5-50:1, for example 10-40:1 or 20-30:1. In an embodiment, the alkylation feedstock is a hydrocarbon fraction containing C3-C6 alkanes and C3-C6 alkenes, wherein the mole ratio of alkane to alkene is 5-50:1, for example 10-40:1 or 20-30:1. In an embodiment, the alkylation feedstock is a mixture of C3-C6 alkanes and C3-C6 alkenes, wherein the mole ratio of alkane to alkene is 5-50:1, for example 10-40:1 or 20-30:1.

According to the solid acid alkylation process of the present invention, isoalkanes and alkenes in the stream entering each catalyst bed can be those conventionally selected in the prior art. Preferably, the molar ratio of isoalkane to alkene in the stream entering each catalyst bed (namely, alkane/alkene ratio) is 200-1000:1. In this way, not only can the alkene be completely or substantially completely converted, but also higher product selectivity can be obtained, and at the same time, the alkylation catalyst can have higher activity and stability. Preferably, the molar ratio of isoalkane to alkene in the stream entering each catalyst bed is 400-750:1.

According to the present invention, the reaction temperature in the axial moving bed reactor is preferably below the critical temperature of the isoalkane, more preferably not higher than 120° C. (for example 30-120° C.), further preferably not higher than 100° C., further more preferably 30-100° C., for example 60-80° C. For the alkylation reaction conditions, the pressure generally can be 1-3.4 MPa, preferably 1.2-3.2 MPa, for example 1.5-3.0 MPa.

The pressure is gauge pressure.

According to the present invention, the weight hourly space velocity of the stream entering each catalyst bed based on the alkene can be 0.05-1 h$^{-1}$, preferably 0.07-0.5 h$^{-1}$, for example 0.08-0.25 h$^{-1}$.

According to a preferred embodiment of the present invention, the residence time of the catalyst in the axial moving bed reactor is 6-72 hours, preferably 12-72 hours.

According to the process provided by the present invention, the catalyst is not particularly limited, can be a variety of catalysts conventionally used in the art, for example can be a solid acid catalyst.

Preferably, the solid acid catalyst contains a molecule sieve and a heat-resistant inorganic oxide. Based on the total amount of the solid acid catalyst, the content of the molecule sieve is 65-95 wt %, more preferably 65-90 wt %, and the content of the inorganic oxide is 5-35 wt %, more preferably 10-35 wt %.

Further preferably, the molecule sieve is selected from at least one of FAU structure zeolite, BETA structure zeolite and MFI structure zeolite.

In the present invention, the heat-resistant inorganic oxide refers to an inorganic oxide whose maximum service temperature is not less than 600° C. The heat-resistant inorganic oxide may be alumina and/or silica.

In one more preferred embodiment of the present invention, the solid acid catalyst further contains a metal active component, the metal active component is selected from at least one of Fe, Co, Ni, Pd and Pt, based on the total amount of the solid acid catalyst, the content of the metal active component is 0.15-2 wt %. With the catalyst according to this preferred embodiment, under the equal other conditions, longer cycle life and service life can be obtained, and at the same time, higher product selectivity can be obtained.

According to the present invention, the average particle size of the catalyst may be 0.3-3 mm.

In the present invention, the catalyst bed is also called the reaction bed, two adjacent catalyst beds means an upstream reaction bed and a downstream reaction bed thereof; If the catalyst regeneration bed is not included, two adjacent catalyst beds means two upstream and downstream catalyst beds, While if a catalyst regeneration bed that is not the last bed is included, two adjacent catalyst beds means a catalyst bed (namely the reaction bed) that is the first bed upstream the catalyst regeneration bed but not a catalyst regeneration bed, and a catalyst bed (namely the reaction bed) that is the first bed downstream the catalyst regeneration bed but not a catalyst regeneration bed respectively.

In the present invention, between two adjacent beds means between any two adjacent beds, comprising: between an upstream catalyst bed (namely the reaction bed) and a downstream catalyst bed (namely the reaction bed), between an upstream catalyst bed (namely the reaction bed) and a downstream catalyst regeneration bed, between an upstream catalyst regeneration bed and a downstream catalyst bed (namely the reaction bed), between an upstream catalyst regeneration bed and a downstream catalyst regeneration bed.

According to a preferred embodiment of the present invention, a separation component 10 is arranged between two adjacent catalyst beds 3 and if any, between the upstream catalyst bed (reaction bed) and the last catalyst regeneration bed, for example, a separation component 10 may be arranged in each reaction bed, the inside space of the separation component 10 is communicated with the catalyst delivery pipe 16, the separation component 10 is for separating the stream after the reaction in the upstream catalyst bed from the catalyst, the catalyst obtained by the separation with the separation component 10 moves down through the catalyst delivery pipe 16. The stream after the reaction in the upstream catalyst bed and the catalyst are separated with the separation component 10 to give the stream after the reaction and the catalyst, the catalyst moves down through the catalyst delivery pipe 16, while the stream after the reaction is mixed with a liquid-state fresh reaction feedstock that is introduced through the feed inlet above the catalyst bed 3 in the space between two adjacent catalyst beds (in the present invention, it is called the bed space before the reaction bed), and then the resulting mixture flows into the downstream catalyst bed.

According to a specific embodiment of the present invention, the separation component 10 may be a screen mesh with holes (the hole diameter may be determined according to the size of the catalyst particles), which allows the stream after the reaction to pass through, so as to realize the separation of the stream after the reaction and the catalyst.

In order to achieve a more uniform mixing of the stream after the reaction and the liquid-state fresh reaction feedstock that flow into the downstream catalyst bed, preferably, a reaction stream deflector 11 is arranged between two adjacent catalyst beds 3, the reaction stream deflector 11 is for intensifying the mixing of the stream after the reaction and the liquid-state fresh reaction feedstock fed through the feed inlets 2. For example, a reaction stream deflector may be arranged in each catalyst bed, especially in the bed space of the reaction bed.

In the present invention, the specific structure of the reaction stream deflector 11 is not particularly limited, as long as it can intensify the mixing of the stream after the reaction and the liquid-state fresh reaction feedstock. Specifically, the reaction stream deflector 11 is placed in the bed space before the reaction bed, and its number can be one or two or more, preferably 1-6.

According to the first preferred embodiment of the present invention, as shown in FIG. 2, the reaction stream deflector 11 includes a main axis 111 and a delivering element 112 extending spirally along the axial direction of the main axis. Specifically, the inlet of the spirally extending flow channel formed by the delivering element 112 is set according to the position of the feed inlet 2 so that the stream after the reaction and the liquid-state fresh reaction feedstock flow along the spirally extending flow channel formed by the delivering element 112 to achieve the mixing.

According to the second preferred embodiment of the present invention, as shown in FIG. 1, the reaction stream deflector 11 comprises a plurality of deflecting plates 113, a plurality of deflecting plates 113 are inclined along the axial direction of the axial moving bed reactor 1, and a plurality of deflecting plates 113 are arranged in a staggered manner with each other to form a flow channel through which the reaction stream can pass. A plurality of the deflecting plates 113 can be inclined downwards or upwards along the axial direction of the axial moving bed reactor 1 (as shown in FIG. 1). Preferably, the angle between the extension direction of the deflecting plate 113 and the horizontal plane is 5-60 degrees, further preferably 10-40 degrees.

The deflecting plates 113 arranged in a staggered manner with each other as mentioned in the present invention means the deflecting plates 113 do not form a closed area in relation to each other, so that the reaction stream can flow downward smoothly. According to a specific embodiment of the present invention, as shown in FIG. 1, a part of the deflecting plates 113 are fixedly connected to the wall of the axial moving bed reactor 1, and a part of the deflecting plates 113 are fixedly connected to the wall of the catalyst delivery pipe 16, and the deflecting plates 113 are arranged parallel to each other. Preferably, the distance between the deflecting plates 113 is 15-60 mm.

According to a preferred embodiment of the present invention, between two adjacent catalyst beds 3 and if a catalyst regeneration bed is present, between two adjacent beds, is arranged a catalyst distribution component, which is for dispersing the catalyst at the outlet of the catalyst delivery pipe 16. If no catalyst distribution component is arranged, the catalyst at the outlet of the catalyst delivery pipe 16 is likely to form a cone-shaped accumulation on the downstream catalyst bed. Preferably, the catalyst distribution component comprises a cone-shaped distribution baffle 12, and the cone-shaped distribution baffle 12 is arranged coaxially with the catalyst delivery pipe 16. The catalyst at the outlet of the catalyst delivery pipe 16 falls on the tip of the cone-shaped distribution baffle 12 by gravity, and is dispersed to the horizontal sides of the catalyst delivery pipe 16 under the dispersion action of the cone-shaped distribution baffle 12. Further preferably, the number of the cone-shaped distribution baffle 12 is identical to the number of the catalyst delivery pipe 16.

According to a preferred embodiment of the present invention, the catalyst distribution component further comprises a horizontal distribution baffle 13 arranged below the cone-shaped distribution baffle 12, and the horizontal distribution baffle 13 is provided with holes through which the catalyst can pass. The number of the horizontal distribution baffle 13 is not particularly limited by the present invention, and can be one or two or more, and preferably the horizontal distribution baffle 13 is each arranged in the radial middle position of (and in the axial direction, below) two adjacent cone-shaped distribution baffles 12. The radial direction and the axial direction refers to the radial direction and the axial direction of the axial moving bed reactor 1.

Further preferably, in the horizontally outward direction from the center of the axial moving bed reactor 1, the holes of the horizontal distribution baffle 13 gradually become larger. With this preferred embodiment, a part of the catalyst that is close to the center position of the axial moving bed reactor 1 and dispersed by means of the cone-shaped distribution baffle 12 is passed through the holes of the horizontal distribution baffle 13, and another part of the catalyst that cannot pass through is dispersed to the edge position of the axial moving bed reactor 1, which is more conducive to ensuring the uniform dispersion of the catalyst.

Further preferably, the horizontal distribution baffle 13 may be a circular distribution plate with a low opening rate in the center area and a high opening rate at the edge wall.

The catalyst in each catalyst bed of the axial moving bed reactor 1 gradually deactivates and gradually falls to a further downstream catalyst bed (reaction bed) or catalyst regeneration bed along with the reaction, finally reaches the bottom of the axial moving bed reactor 1, and then is delivered to the spent catalyst receiver 5 through the catalyst delivery pipeline.

According to a preferred embodiment of the present invention, a bottom catalyst-collecting area 37 is provided at the lower part of the axial moving bed reactor 1. The catalyst passing through the most downstream catalyst bed is sent to the bottom catalyst-collecting area 37, and a certain amount of the catalyst is collected and sent to the spent catalyst receiver 5.

According to a specific embodiment of the present invention, as shown in FIG. 1, the stream pipeline valves between the containers are arranged respectively on the communication pipelines of the axial moving bed reactor 1 and the spent catalyst receiver 5, the spent catalyst receiver 5 and the catalyst regenerator 4, the catalyst regenerator 4 and the regenerated catalyst receiver 6, and the regenerated catalyst receiver 6 and the axial moving bed reactor 1.

According to a preferred embodiment of the present invention, the spent catalyst receiver 5 (preferably the bottom) is provided with an outlet for withdrawing the liquid-phase stream 15. According to the present invention, the liquid-phase stream carried in the catalyst can be removed by means of directly reducing the pressure or increasing the pressure by introducing high-pressure hydrogen, nitrogen and the like in the spent catalyst receiver 5, and the liquid-phase stream can be discharged through the outlet for withdrawing the liquid-phase stream 15. Preferably, a removed liquid filter 7 is arranged on a delivery pipeline for withdrawing the liquid-phase stream starting from the outlet for withdrawing the liquid-phase stream 15. The removed liquid filter 7 is used to block fine catalyst powder or fine catalyst particles.

The liquid-withdrawn catalyst in the spent catalyst receiver 5 is sent to the catalyst regenerator 4 for regeneration. The catalyst regenerator 4 is provided with an inlet for feeding the regeneration medium 30 and an outlet for discharging the regeneration medium 31. The regeneration medium is introduced into the catalyst regenerator 4 through the inlet for feeding the regeneration medium 30 and contacted with the catalyst for the regeneration of the catalyst (preferably full regeneration), and the regeneration medium is discharged through the outlet for discharging the regeneration medium 31. Preferably, a medium-after-regeneration filter 8 is arranged on a regeneration medium delivery pipeline starting from the outlet for discharging the regeneration medium 31. The filter is used to block the catalyst of the regenerator from flowing into the downstream gas circulation pressurizing equipment and to collect the fine powder or fine particles generated during the regeneration process due to friction or purging.

According to the process of the present invention, the manner of regeneration in the catalyst regenerator 4 is not particularly limited, and it can be performed under normal regeneration conditions. The regeneration medium may be an oxygen-containing atmosphere or a hydrogen-containing atmosphere. Specifically, the regeneration may be performed in a hydrogen-containing atmosphere, or may be performed in an oxygen-containing atmosphere. The oxygen-containing atmosphere contains oxygen and an optional carrier gas. The carrier gas may be selected from inactive gas, and specific examples thereof can include, but are not limited to, nitrogen gas and Group Zero element gases (such as argon). In the oxygen-containing atmosphere, the content of oxygen gas may be 0.5-20% by volume. In addition, the content of oxygen gas can also be adjusted according to the regeneration process. The hydrogen-containing atmosphere may contain hydrogen gas and C4 liquefied gas, and the content of hydrogen gas is 70-99% by volume.

As an example of the regeneration in the catalyst regenerator 4, the regeneration is carried out in a hydrogen atmosphere, and the regeneration can be carried out at a temperature of 100-400° C., preferably 180-280° C.; during the regeneration, the pressure in the reactor may be 0.1-5 MPa, preferably 0.5-3.5 MPa, the pressure is gauge pressure. As another example of the regeneration, the regeneration is carried out in an oxygen-containing atmosphere, and the regeneration can be carried out at a temperature of 180-500° C.; during regeneration, the pressure in the reactor can be 0.01-0.5 MPa, and the pressure is gauge pressure.

According to the present invention, preferably, the superficial flow velocity of the regeneration medium in the catalyst regenerator 4 is 0.003-0.8 m/s, further preferably 0.02-0.5 m/s.

In the present invention, the regeneration in the catalyst regenerator 4 is also referred to as high temperature regeneration.

According to a preferred embodiment of the present invention, the process further comprises: introducing a fresh catalyst into the catalyst regenerator 4. Specifically, the catalyst regenerator 4 may be provided with a fresh catalyst feed inlet for the fresh catalyst to enter the catalyst regenerator 4. By providing the catalyst regenerator 4 with the fresh catalyst feed inlet, a part of the catalyst that has lost its activity or the catalyst that is difficult to restore the initial activity can be replaced with a fresh catalyst to ensure the processing capacity of the apparatus. Specifically, a pump is provided on the fresh catalyst delivery pipeline communicating with the fresh catalyst feed inlet.

The regenerated catalyst will flow into the regenerated catalyst receiver 6 through the catalyst delivery pipeline at the bottom of the catalyst regenerator 4.

According to a preferred embodiment of the present invention, the process also comprises using a liquid-phase stream to replace the gas in the gap of the catalyst in the regenerated catalyst receiver 6. Specifically, the regenerated catalyst receiver 6 is provided with an inlet for supplementing the liquid-phase stream 32. A liquid-phase stream is introduced to the regenerated catalyst receiver 6 through the inlet for supplementing the liquid-phase stream 32 to replace the gas in the gap of the catalyst. The present invention has no particular limitation on the liquid-phase stream. For example, it may be an alkane or a reaction product obtained from the bottom of the axial moving bed reactor 1.

The regenerated catalyst will return to the axial moving bed reactor 1 through the catalyst delivery conduit between the regenerated catalyst receiver 6 and the axial moving bed reactor 1, and continue to participate in the reaction until it is deactivated and transported to the spent catalyst receiver 5. The catalyst is circulated according to the above protocol.

According to a preferred embodiment of the present invention, the spent catalyst receiver 5, the catalyst regenerator 4 and the regenerated catalyst receiver 6 are successively arranged from top to bottom, catalyst circulation pipelines for connecting the spent catalyst receiver 5, the catalyst regenerator 4 and the regenerated catalyst receiver 6 are arranged vertically or inclined at an angle relative to the horizontal plane of not less than 40 degrees. Using this preferred embodiment is more convenient for the smooth flow of the stream of catalyst particles from top to bottom, and prevents the stream from accumulating or remaining in the pipeline, which affects the valve sealing performance or the catalyst regeneration effect.

According to a preferred embodiment of the present invention, on the communication pipeline of the catalyst outlet of the axial moving bed reactor 1 and the catalyst inlet of the spent catalyst receiver 5 is arranged a first particle flow regulator 25; and on the communication pipeline of the catalyst outlet of the regenerated catalyst receiver 6 and the catalyst inlet of the axial moving bed reactor 1 is arranged a second particle flow regulator 33. The first particle flow regulator 25 and the second particle flow regulator 33 is not particularly limited by the present invention, as long as the flow rate of the catalyst particles can be adjusted. Further preferably, the first particle flow regulator 25 and the second particle flow regulator 33 each independently are L-shaped or approximately L-shaped stream transportation valve set.

Specifically, the L-shaped or approximately L-shaped stream transportation valve set is also communicated with at least one liquid-phase stream feeding pipeline. Arranging the particle flow regulator can increase the flow resistance of the particle stream. At the same time, the regulator is communicated with at least one liquid-phase stream feeding pipeline to increase the flow driving force of the particle stream and reduce the flow resistance of the particle stream. By arranging L-shaped or approximately L-shaped stream transportation valve set and by changing the flow of the liquid-phase stream entering the valve set, the discharge rate of the catalyst can be adjusted, so that the falling rate and the residence time in each reaction bed of the catalyst in the reactor can be controlled and adjusted.

According to a preferred embodiment of the present invention, the apparatus further comprises a catalyst buffer tank 38, the catalyst buffer tank 38 is arranged between the axial moving bed reactor 1 and the spent catalyst receiver 5, the catalyst inlet of the catalyst buffer tank 38 is communicated with the catalyst outlet of the axial moving bed reactor 1, and the catalyst outlet of the catalyst buffer tank 38 is communicated with the catalyst inlet of the spent catalyst receiver 5. The catalyst buffer tank 38 is used for storing the catalyst discharged from the axial moving bed reactor 1 during the periods of withdrawing the liquid-phase stream from the spent catalyst receiver and discharging the catalyst to the catalyst regenerator, ensuring the flow continuity of the catalyst stream in the axial moving bed reactor 1 and the smoothness of the apparatus operation.

In an embodiment of the present invention, the axial moving bed reactor comprises:

At least one, preferably, at least two catalyst beds (also known as reaction beds) and at least one catalyst regeneration bed, preferably, the reaction bed number is identical to the catalyst regeneration bed number and the reaction beds 51, 53 and the catalyst regeneration beds 52, 54 are intervally successively arranged, more preferably the number of the catalyst regeneration bed is one less than the number of the catalyst bed, the catalyst bed and the catalyst regeneration bed are intervally successively arranged, and the catalyst reaction beds are arranged both at the top and the bottom of the axial moving bed reactor;

The axial moving bed reactor has a catalyst inlet 62, which is communicated with the top of the first reaction bed;

There are a catalyst inlet and an inlet for feeding the reaction stream 60 at the top of each reaction bed, the catalyst inlet of the first reaction bed is the catalyst inlet of the axial moving bed reactor, and the catalyst inlet of the subsequent reaction bed is communicated with the catalyst delivery pipe;

There are the catalyst outlets communicated with the catalyst delivery conduits 63, 65 and the reaction stream outlets 59, 61 at the bottom of each reaction bed.

There are the catalyst inlets communicated with the catalyst delivery conduits 63, 65 and the regenerating medium outlets 68, 71 at the top of the catalyst regeneration bed;

There are the catalyst outlets communicated with the catalyst delivery conduit 64, 66 and the regenerating medium outlets 67, 69 at the bottom of the catalyst regeneration bed;

An isolation medium inlet 70 is arranged on the catalyst delivery pipeline for transferring the catalyst from the catalyst regeneration bed to the catalyst bed;

A separation component 72 is arranged at the bottom of each reaction bed;

Various beds are communicated with each other through the catalyst delivery pipeline;

The bottom of the catalyst bed and the regeneration bed are communicated by means of a catalyst delivery conduit that is inserted into the interior of the regeneration bed, the outlet of the inserted-type catalyst delivery conduit is below the regeneration medium outlet in the regeneration bed;

The isolation medium is preferably a recycled stream pressurized by a pump after the reaction. Therefore, the isolation medium inlet 70 is communicated with the reaction stream outlet 61 of the last reaction bed;

The stream after the reaction passes through the separation component 72 to enter the next reaction bed or be finally discharged, and the catalyst that does not pass through the separation component 72 moves down through the catalyst delivery pipe;

The reaction stream outlet 59 of the upstream reaction bed is communicated with the inlet for feeding the reaction stream 60 of the downstream reaction bed through a pipeline, and the communication pipeline is also provided with fresh reaction feedstock inlet(s) 56, 57;

The top of the bed refers to being located at 70% or higher of each bed from bottom to top, and the bottom of the bed refers to being located at 20% or lower of each bed from bottom to top;

The regeneration medium outlet 68 of the upstream catalyst regeneration bed is communicated with the regeneration medium inlet 69 of the downstream catalyst regeneration bed through a pipeline;

The inlet for feeding the reaction stream 60 of the reaction bed, the regeneration medium inlet of the catalyst regeneration bed, and the isolation medium inlet 70 arranged on the catalyst delivery pipeline for transferring the catalyst from the catalyst regeneration bed to the catalyst bed are provided with the corresponding stream distributor.

In an embodiment of the present invention, the process comprises: the liquid-state fresh reaction feedstock 55 and the recycled stream 58 or the stream after the reaction in the upstream the reaction bed are mixed and the resulting mixture enters the reaction bed of the axial moving bed; In the reaction bed, after the distribution with the reaction stream distributor, the mixed stream passes through the reaction bed along the axial direction of the reaction bed, contacts with the solid acid catalyst to perform the reaction, after the completion of the reaction, the majority (>90 vol %, or >95 vol %, or >96 vol %, or >97 vol %, or >98 vol %, or >99 vol %) of the liquid-phase stream leaves this bed through the arranged reaction stream outlet, while the minority of the remaining liquid-phase stream, together with the catalyst particles, enters the catalyst regeneration bed through the inserted-type conduit between the reaction bed and the catalyst regeneration bed; The discharged liquid-phase stream after the reaction enters the next reaction bed after mixing with the fresh reaction feedstock to continue to participate in the reaction or directly leaves the reaction bed, and the alkylation oil product is collected after the separation (e.g., distillation); In the catalyst regeneration bed, the catalyst contacts in countercurrent with a liquid-phase regeneration medium in which hydrogen is dissolved under the regeneration condition (also referred to as low-temperature regeneration herein), so that unsaturated hydrocarbons adsorbed on the catalyst are converted into saturated hydrocarbon molecules which are easy to desorb and are taken out of the catalyst regeneration bed to realize the partial regeneration of the catalyst;

The regenerated catalyst will flow into the next reaction bed through the catalyst delivery pipeline at the bottom of the catalyst regeneration bed;

During the course of transporting the catalyst from the bottom of the catalyst regeneration bed to the reaction bed, the isolation medium enters through the isolation medium inlet arranged on the delivery pipeline and replaces the liquid-phase medium that is descending together with the catalyst; The inactivation degree of the catalyst in each bed (reaction bed and catalyst regeneration bed) of the moving bed gradually increases along with the reaction and the increased regeneration number, and meanwhile the catalyst also gradually falls to the lower bed (reaction bed or catalyst regeneration bed) and finally reaches the bottom of the moving bed reactor; Finally, the catalyst is sent to the catalyst regenerator 4 (for high-temperature deep regeneration) to realize the complete recovery of the catalyst activity; The catalyst with the recovered activity is sent to the first reaction bed of the moving bed reactor to continuously participate in the reaction, and the process is circulated in this manner;

The reaction conditions in the reaction bed may include:
The reaction temperature is 30-100° C.,
The reaction pressure is 1.0-3.4 MPa, gauge pressure,
The superficial flow velocity of the liquid-phase stream in the reactor is 0.03-1 m/s;
The weight hourly space velocity of the mixed alkene feedstock is 0.05-1 $h^{-1}$;
The mole ratio of alkane to alkene at the reaction bed inlet is 200-1000:1;
The average particle diameter of the solid acid catalyst particles is 0.3-3 mm.

The regeneration conditions in the catalyst regeneration bed can comprise:
The regeneration temperature is 50-140° C.,
The superficial flow velocity of the regeneration medium in the regenerator is 0.01-0.5 m/s;
The regeneration medium is a liquid hydrocarbon in which hydrogen is dissolved; the liquid hydrocarbon is C3-C6 (for example C3-C5) saturated alkanes or a mixture of the reaction product and the above-mentioned saturated alkanes, Preferably, the liquid hydrocarbon is a mixture of C3-C6 (for example C3-C5) saturated alkanes and the reaction product;

The regeneration conditions in the catalyst regenerator (high temperature deep regeneration) may include:
The regeneration temperature is 180-400° C.,
The regeneration pressure is 0.5-4.0 MPa,
The regeneration medium is hydrogen gas or a mixture of hydrogen gas and low carbon hydrocarbon (for example C3-C8), preferably a mixture of hydrogen gas and low carbon hydrocarbon (for example C3-C8);

The main active component of the catalyst is a molecule sieve loaded with a certain amount of metal, the molecule sieve is one of or a combination of two or more of FAU structure zeolite, BETA structure zeolite, MFI structure zeolite, preferably a zeolite having FAU structure and a zeolite having BETA structure, the metal loaded on the catalyst is one of or a combination of two or more of Fe, Co, Ni, Pd and/or Pt, preferably one of or a combination of two or more of Co, Ni or Pt.

The process provided by the present invention adopts a liquid-solid axial moving bed reaction and regeneration apparatus, can realize the continuous and stable operation of the solid acid alkylation reaction and the regeneration of the deactivated catalyst, improves the selectivity of the target product and the flexibility of the apparatus operation, greatly reduces the catalyst investment cost, and improves the economic competitiveness of the apparatus.

In addition, the present invention provides a set of the following technical solutions:

1. A liquid-solid axial moving bed reaction and regeneration apparatus, which is characterized in that the apparatus comprises:

An axial moving bed reactor, a spent catalyst receiver, a catalyst regenerator and a regenerated catalyst receiver that are successively connected, wherein a catalyst outlet of the regenerated catalyst receiver is communicated with a catalyst inlet of the axial moving bed reactor;

Wherein, the axial moving bed reactor is provided with at least two catalyst beds arranged up and down, the axial moving bed reactor is provided with a feed inlet above each catalyst bed;

A catalyst delivery pipe is arranged between two adjacent catalyst beds, so that the catalyst can move from top to bottom in the axial moving bed reactor.

2. The liquid-solid axial moving bed reaction and regeneration apparatus according to technical solution 1, wherein the reaction stream outlet of the axial moving bed reactor is communicated with the uppermost feed inlet of the axial moving bed reactor so as to recycle the reaction stream obtained from the axial moving bed reactor back to the axial moving bed reactor.

3. The liquid-solid axial moving bed reaction and regeneration apparatus according to technical solution 1, wherein A separation component is arranged between two adjacent catalyst beds, and the separation component is communicated with the catalyst delivery pipe;

the separation component is for separating the stream after the reaction in the upstream catalyst bed from the catalyst, the catalyst obtained from separation with the separation component moves down through the catalyst delivery pipe.

4. The liquid-solid axial moving bed reaction and regeneration apparatus according to any of technical solutions 1-3, wherein a reaction stream deflector is arranged between two adjacent catalyst beds, and the reaction stream deflector is used to intensify the mixing of the stream after the reaction and the liquid-state fresh feedstock from the feed inlet.

5. The liquid-solid axial moving bed reaction and regeneration apparatus according to technical solution 4, wherein the reaction stream deflector comprises a main axis (111) and a delivering element (112) extending spirally along the axial direction of the main axis.

6. The liquid-solid axial moving bed reaction and regeneration apparatus according to technical solution 4, wherein the reaction stream deflector includes a plurality of deflecting plates (113), and a plurality of deflecting plates (113) are inclined along the axial direction of the axial moving bed reactor, and a plurality of deflecting plates (113) are arranged in a staggered manner with each other to form a flow channel through which the reaction stream can pass.

7. The liquid-solid axial moving bed reaction and regeneration apparatus according to any of technical solutions 1-6, wherein a catalyst distribution component is arranged between two adjacent catalyst beds, and the catalyst distribution component is used to disperse the catalyst at the outlet of the catalyst delivery pipe;

Preferably, the catalyst distribution component includes a cone-shaped distribution baffle, and the cone-shaped distribution baffle is arranged coaxially with the catalyst delivery pipe; further preferably, the number of the cone-shaped distribution baffle is identical to the number of the catalyst delivery pipe;

Further preferably, the catalyst distribution component further comprises a horizontal distribution baffle arranged below the cone-shaped distribution baffle, and the horizontal distribution baffle is provided with holes through which the catalyst can pass.

8. The liquid-solid axial moving bed reaction and regeneration apparatus according to any of technical solutions 1-7, wherein the catalyst regenerator is provided with a fresh catalyst feed inlet for the fresh catalyst to enter the catalyst regenerator.

9. The liquid-solid axial moving bed reaction and regeneration apparatus according to any of technical solutions 1-8, wherein a spent catalyst receiver, a catalyst regenerator and a regenerated catalyst receiver are successively arranged from top to bottom, and catalyst circulation pipelines for connecting the spent catalyst receiver, the catalyst regenerator and the regenerated catalyst receiver are arranged vertically or inclined at an angle relative to the horizontal plane of not less than 40 degrees.

10. The liquid-solid axial moving bed reaction and regeneration apparatus according to any of technical solutions 1-9, wherein a first particle flow regulator is provided on the communication pipeline of the catalyst outlet of the axial moving bed reactor and the catalyst inlet of the spent catalyst receiver; a second particle flow regulator is provided on the communication pipeline of the catalyst outlet of the regenerated catalyst receiver and the catalyst inlet of the axial moving bed reactor;

Preferably, the first particle flow regulator and the second particle flow regulator are each independently L-shaped or approximately L-shaped stream transportation valve set.

11. The liquid-solid axial moving bed reaction and regeneration apparatus according to any of technical solutions 1-10, wherein the apparatus further comprises a catalyst buffer tank, the catalyst buffer tank is arranged between the axial moving bed reactor and the spent catalyst receiver, the catalyst inlet of the catalyst buffer tank is communicated with the catalyst outlet of the axial moving bed reactor, and the catalyst outlet of the catalyst buffer tank is communicated with the catalyst inlet of the spent catalyst receiver.

12. Use of the liquid-solid axial moving bed reaction and regeneration apparatus according to any of technical solutions 1-11 in the solid acid alkylation reaction.

In addition, the present invention provides another group of the following technical solutions:

1. A solid acid alkylation process, comprising:

The process is performed in a liquid-solid axial moving bed reaction and regeneration apparatus, the liquid-solid axial moving bed reaction and regeneration apparatus comprises an axial moving bed reactor, a spent catalyst receiver, a catalyst regenerator and a regenerated catalyst receiver that are successively connected, wherein a catalyst outlet of the regenerated catalyst receiver is communicated with a catalyst inlet of the axial moving bed reactor; the axial moving bed reactor is provided with at least two catalyst beds arranged up and down, the axial moving bed reactor is provided with a feed inlet above each catalyst bed; a catalyst delivery pipe is arranged between two adjacent catalyst beds, so that the catalyst can move from top to bottom in the axial moving bed reactor;

The liquid-phase feedstock is sent into the axial moving bed reactor from the feed inlet above each catalyst bed and contacted with the catalyst to perform the reaction.

2. The process according to technical solution 1, wherein the process further comprises: the reaction product obtained at the bottom of the axial moving bed reactor is recycled to a position above the uppermost upstream catalyst bed and mixed with the liquid-phase feedstock and then fed into the reactor.

3. The process according to technical solution 1 or 2, wherein in the axial moving bed reactor, the reaction temperature is 30-100° C., and the pressure is 1-3.4 MPa;

Preferably, the weight hourly space velocity of the stream entering each catalyst bed based on the alkene is 0.05-1 $h^{-1}$;

Preferably, the molar ratio of isoalkane to alkene in the stream entering each catalyst bed is 200-1000:1;

Preferably, the residence time of the catalyst in the axial moving bed reactor is 6-72 h.

4. The process according to any of technical solutions 1-3, wherein the catalyst is a solid acid catalyst, the solid acid catalyst contains a molecule sieve and a heat-resistant inorganic oxide, based on the total amount of the solid acid catalyst, the content of the molecule sieve is 65-95 wt %, the content of the heat-resistant inorganic oxide is 5-35 wt %;

Preferably, the molecule sieve is selected from at least one of FAU structure zeolite, BETA structure zeolite and MFI structure zeolite, the heat-resistant inorganic oxide is alumina and/or silica;

Further preferably, the solid acid catalyst further contains a metal active component, the metal active component is selected from at least one of Fe, Co, Ni, Pd and Pt, based on the total amount of the solid acid catalyst, the content of the metal active component is 0.15-2 wt %.

5. The process according to any of technical solutions 1-4, wherein a separation component is arranged between two adjacent catalyst beds, and the separation component is communicated with the catalyst delivery pipe; the separation component is for separating the stream after the reaction in the upstream catalyst bed from the catalyst, the catalyst obtained from separation with the separation component moves down through the catalyst delivery pipe.

6. The process according to any of technical solutions 1-5, wherein a reaction stream deflector is arranged between two adjacent catalyst beds, and the reaction stream deflector is used to intensify the mixing of the stream after the reaction and the liquid-state fresh feedstock from the feed inlet.

Preferably, the reaction stream deflector comprises a main axis (111) and a delivering element (112) extending spirally along the axial direction of the main axis.

Preferably, the reaction stream deflector comprises a plurality of deflecting plates (113), and a plurality of deflecting plates (113) are inclined along the axial direction of the axial moving bed reactor, and a plurality of deflecting plates (113) are arranged in a staggered manner with each other to form a flow channel through which the reaction stream can pass.

7. The process according to any of technical solutions 1-6, wherein a catalyst distribution component is arranged between two adjacent catalyst beds, and the catalyst distribution component is used to disperse the catalyst at the outlet of the catalyst delivery pipe;

Preferably, the catalyst distribution component includes a cone-shaped distribution baffle, and the cone-shaped distribution baffle is arranged coaxially with the catalyst delivery pipe; further preferably, the number of the cone-shaped distribution baffle is identical to the number of the catalyst delivery pipe;

Further preferably, the catalyst distribution component further comprises a horizontal distribution baffle arranged below the cone-shaped distribution baffle, and the horizontal distribution baffle is provided with holes through which the catalyst can pass.

8. The process according to any of technical solutions 1-7, wherein the catalyst at the bottom of the axial moving bed reactor is transported to the spent catalyst receiver to remove the liquid-phase stream carried in the catalyst, and then transported to the catalyst regenerator for regeneration;

Preferably, the superficial flow velocity of the regeneration medium in the catalyst regenerator is 0.003-0.8 m/s, further preferably 0.02-0.5 m/s.

9. The process according to any of technical solutions 1-8, wherein the catalyst regenerator is provided with a fresh catalyst feed inlet for the fresh catalyst to enter the catalyst regenerator.

10. The process according to any of technical solutions 1-9, wherein a spent catalyst receiver, a catalyst regenerator and a regenerated catalyst receiver are successively arranged from top to bottom, and catalyst circulation pipelines for connecting the spent catalyst receiver, the catalyst regenerator and the regenerated catalyst receiver are arranged vertically or inclined at an angle relative to the horizontal plane of not less than 40 degrees.

11. The process according to any of technical solutions 1-10, wherein a first particle flow regulator is provided on the communication pipeline of the catalyst outlet of the axial moving bed reactor and the catalyst inlet of the spent catalyst receiver; a second particle flow regulator is provided on the communication pipeline of the catalyst outlet of the regenerated catalyst receiver and the catalyst inlet of the axial moving bed reactor;

Preferably, the first particle flow regulator and the second particle flow regulator are each independently L-shaped or approximately L-shaped stream transportation valve set.

12. The process according to any of technical solutions 1-11, wherein the apparatus further comprises a catalyst buffer tank, the catalyst buffer tank is arranged between the axial moving bed reactor and the spent catalyst receiver, the catalyst inlet of the catalyst buffer tank is communicated with the catalyst outlet of the axial moving bed reactor, the catalyst outlet of the catalyst buffer tank is communicated with the catalyst inlet of the spent catalyst receiver.

Hereinafter in conjunction with the accompanying drawings, the specific examples or embodiments of the liquid-solid axial moving bed reaction and regeneration apparatus and the solid acid alkylation process provided by the present invention will be illustrated, but the present invention is not limited thereto.

As shown in FIG. 1, the axial moving bed reactor 1 is provided with three catalyst beds 3, the spent catalyst receiver 5, the catalyst regenerator 4 and the regenerated catalyst receiver 6 are successively arranged from top to bottom, and the catalyst circulation pipelines of these three are arranged vertically.

The isobutane-containing fresh alkene feedstock is introduced from the line 17, passed through the first branch pipeline 19 and mixed with the recycled material, and then the mixture enters the reaction zone of the axial moving bed reactor 1 from the feed inlet 2 to contact with the first catalyst bed 3 to perform the reaction; the fresh alkene feedstocks passing through the second branch pipeline 20 and the third branch pipeline 21 are introduced from the feed inlets 2 and mixed with the stream after the reaction in the upstream catalyst bed in the bed spaces before the reaction bed of the axial moving bed reactor 1.

A separation component 10 is arranged between two adjacent catalyst beds 3, the stream after the reaction passes through the separation component 10, and the catalyst that does not pass through the separation component 10 moves down through the catalyst delivery pipe 16.

A reaction stream deflector 11 is arranged between two adjacent catalyst beds 3, and the mixing of the stream after the reaction passing through the separation component 10 and the fresh reaction feedstock is intensified under the action of the reaction stream deflector 11.

Between two adjacent catalyst beds 3 is further arranged the catalyst distribution component (including the cone-shaped distribution baffle 12 arranged coaxially with the catalyst delivery pipe 16 and the horizontal distribution baffle 13 arranged below the cone-shaped distribution baffle 12).

The catalyst at the outlet of the catalyst delivery pipe 16 is dispersed under the action of the catalyst distribution component and falls to the downstream catalyst bed 3.

The lower part of the axial moving bed reactor 1 is provided with a bottom catalyst-collecting area 37. The catalyst passing through the most downstream catalyst bed is sent to the bottom catalyst-collecting area 37, and a certain amount of the catalyst is collected and sent to the spent catalyst receiver 5.

On the communication pipeline of the catalyst outlet of the axial moving bed reactor 1 and the catalyst inlet of the spent catalyst receiver 5 is arranged the first particle flow regulator 25 to adjust the flow of catalyst particles.

The outlet for withdrawing the liquid-phase stream 15 is arranged at the bottom of the spent catalyst receiver 5, the liquid-phase stream carried in the catalyst is removed in the spent catalyst receiver 5, the removed liquid filter 7 is arranged on the delivery pipeline for withdrawing the liquid-phase stream starting from the outlet for withdrawing the liquid-phase stream 15 to block fine catalyst powder or fine catalyst particles.

The liquid-withdrawn catalyst in the spent catalyst receiver 5 is sent to the catalyst regenerator 4 for regeneration. The catalyst regenerator 4 is provided with the inlet for feeding the regeneration medium 30 and the outlet for discharging the regeneration medium 31. The regeneration medium is introduced into the catalyst regenerator 4 through the inlet for feeding the regeneration medium 30 and contacted with the catalyst for the regeneration of the catalyst, and the regeneration medium is discharged through the outlet for discharging the regeneration medium 31. On the regeneration medium delivery pipeline starting from the outlet for discharging the regeneration medium 31, is arranged a medium-after-regeneration filter 8 to block the fine powder or the fine particles. The catalyst regenerator 4 can also be provided with a fresh catalyst feed inlet for the fresh catalyst to enter the catalyst regenerator 4. By providing the catalyst regenerator 4 with the fresh catalyst feed inlet, a part of the catalyst that has lost its activity or the catalyst that is difficult to restore the initial activity can be replaced with a fresh catalyst to ensure the processing capacity of the apparatus.

The regenerated catalyst flows into the regenerated catalyst receiver 6 through the catalyst delivery pipeline at the bottom of the catalyst regenerator 4, the regenerated catalyst receiver 6 is provided with an inlet for supplementing the liquid-phase stream 32. A liquid-phase stream is introduced to the regenerated catalyst receiver 6 through the inlet for supplementing the liquid-phase stream 32 to replace the gas in the gap of the catalyst.

The regenerated catalyst will return to the axial moving bed reactor 1 through the catalyst delivery conduit between the regenerated catalyst receiver 6 and the axial moving bed reactor 1, and continue to participate in the reaction until it is deactivated and transported to the spent catalyst receiver 5. The catalyst is circulated according to the above protocol. The second particle flow regulator 33 is provided on the communication pipeline of the catalyst outlet of the regenerated catalyst receiver 6 and the catalyst inlet of the axial moving bed reactor 1 to adjust the flow of catalyst particles.

Figure 4:
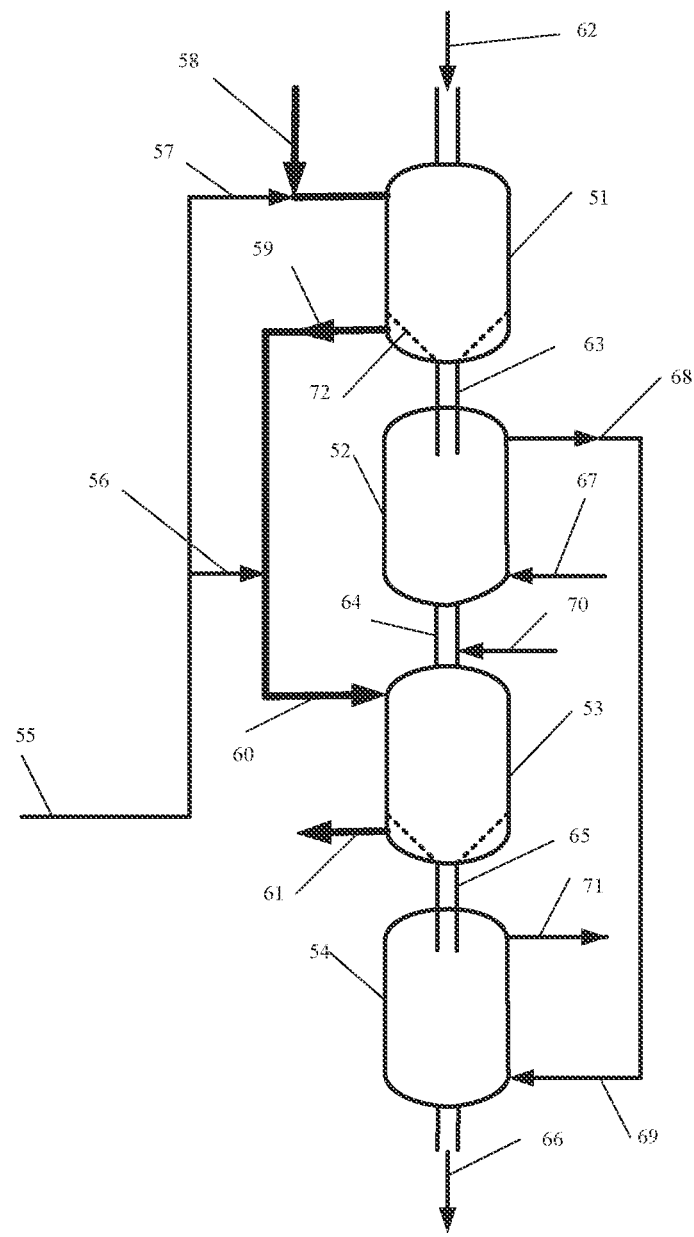
FIG. 4 is a liquid-solid axial moving bed reactor according to a specific embodiment provided by the present invention.

As shown in FIG. 4, in the liquid-solid axial moving bed reaction and regeneration apparatus of the present invention, the axial moving bed reactor comprises the reaction beds 51, 53 and the catalyst regeneration beds 52, 54 that are intervally successively arranged;

The axial moving bed reactor has a catalyst inlet 62, which is communicated with the top of the first reaction bed;

There are a catalyst inlet and an inlet for feeding the reaction stream 60 at the top of the reaction bed;

There are the catalyst outlets communicated with the catalyst delivery conduits 63, 65 and the reaction stream outlets 59, 61 at the bottom of the reaction bed;

There are the catalyst inlets communicated with the catalyst delivery conduits 63, 65 and the regenerating medium outlets 68, 71 at the top of the catalyst regeneration bed;

There are the catalyst outlets communicated with the catalyst delivery conduit 64, 66 and the regenerating medium outlets 67, 69 at the bottom of the catalyst regeneration bed;

An isolation medium inlet 70 is arranged on the catalyst delivery pipeline for transferring the catalyst from the catalyst regeneration bed to the catalyst bed;

A separation component 72 is arranged at the bottom of each reaction bed;

Various beds are communicated with each other through the catalyst delivery pipeline;

The bottom of the catalyst bed and the regeneration bed are communicated by means of a catalyst delivery conduit that is inserted into the interior of the regeneration bed, the outlet of the inserted-type catalyst delivery conduit is below the regeneration medium outlet in the regeneration bed;

The isolation medium is preferably a recycled stream pressurized by a pump after the reaction. Therefore, the isolation medium inlet 70 is communicated with the reaction stream outlet 61 of the last reaction bed;

The stream after the reaction passes through the separation component 72 to enter the next reaction bed or be finally discharged, and the catalyst that does not pass through the separation component 72 moves down through the catalyst delivery pipe;

The reaction stream outlet 59 of the upstream reaction bed is communicated with the inlet for feeding the reaction stream 60 of the downstream reaction bed through a pipeline, and the communication pipeline is also provided with fresh reaction feedstock inlet(s) 56, 57;

The top of the bed refers to being located at 70% or higher of each bed from bottom to top, and the bottom of the bed refers to being located at 20% or lower of each bed from bottom to top;

The regeneration medium outlet 68 of the upstream catalyst regeneration bed is communicated with the regeneration medium inlet 69 of the downstream catalyst regeneration bed through a pipeline;

The inlet for feeding the reaction stream 60 of the reaction bed, the regeneration medium inlet of the catalyst regeneration bed, and the isolation medium inlet 70 arranged on the catalyst delivery pipeline for transferring the catalyst from the catalyst regeneration bed to the catalyst bed are provided with the corresponding stream distributor.

The present invention provides a process of solid acid alkylation reaction and regeneration in presence of hydrogen, wherein the liquid-state fresh reaction feedstock and the recycled stream or the stream after the reaction in the upstream the reaction bed are mixed and enter the reaction bed of the axial moving bed; In the reaction bed, after the distribution with the reaction stream distributor, the mixed stream passes through the reaction bed along the axial direction of the reaction bed, contacts with the solid acid catalyst to perform the reaction, after the completion of the reaction, the majority (>90 vol %, or >95 vol %, or >96 vol %, or >97 vol %, or >98 vol %, or >99 vol %) of the liquid-phase stream leaves this bed through the arranged reaction stream outlet, while the minority of the remaining liquid-phase stream, together with the catalyst particles, enters the catalyst regeneration bed through the inserted-type conduit between the reaction bed and the catalyst regeneration bed; The discharged liquid-phase stream after the reaction enters the next reaction bed after mixing with the fresh reaction feedstock to continue to participate in the reaction or directly leaves the reaction bed, and the alkylation oil product is collected after the separation (e.g., distillation). In the catalyst regeneration bed, the catalyst contacts in countercurrent with a liquid-phase regeneration medium in which hydrogen is dissolved under the regeneration condition (low temperature regeneration), so that unsaturated hydrocarbons adsorbed on the catalyst are converted into saturated hydrocarbon molecules which are easy to desorb and are taken out of the catalyst regeneration bed to realize the partial regeneration of the catalyst; The regenerated catalyst will flow into the next reaction bed through the catalyst delivery pipeline at the bottom of the catalyst regeneration bed; During the course of transporting the catalyst from the bottom of the catalyst regeneration bed to the reaction bed, the isolation medium enters through the isolation medium inlet arranged on the delivery pipeline and replaces the liquid-phase medium that is descending together with the catalyst; The inactivation degree of the catalyst in each bed (reaction bed and catalyst regeneration bed) of the moving bed gradually increases along with the reaction and the increased regeneration number, and meanwhile the catalyst also gradually falls to the lower bed (reaction bed or catalyst regeneration bed) and finally reaches the bottom of the moving bed reactor; Finally, the catalyst is sent to the catalyst regenerator 4 (for high-temperature deep regeneration) to realize the complete recovery of the catalyst activity; The catalyst with the recovered activity is sent to the first reaction bed of the moving bed reactor to continuously participate in the reaction, and the process is circulated in this manner.

The present invention will be described in detail below through examples.

Example 1

This example was performed with the liquid-solid axial moving bed reaction and regeneration apparatus as shown in FIG. 1. Here, the axial moving bed reactor 1, the spent catalyst receiver 5, the catalyst regenerator 4 and the regenerated catalyst receiver 6 were successively connected through pipelines.

The inner diameter of the axial moving bed reactor 1 was 600 mm, and three catalyst beds 3 (denoted as the first catalyst bed, the second catalyst bed, and the third catalyst bed) were arranged from top to bottom. The height of each reaction bed was 1.8 m.

Two cylindrical catalyst delivery pipes 16 were arranged between the first catalyst bed and the second catalyst bed and between the second catalyst bed and the third catalyst bed respectively, and the inner diameter of the catalyst delivery pipe 16 was 20 mm. Separation components 10 (wedge-shaped filter screens with gap width of 0.2 mm) were respectively arranged below the first catalyst bed and below the second catalyst bed. One reaction stream deflector 11, as shown in FIG. 2, was each arranged between the first catalyst bed and the second catalyst bed and between the second catalyst bed and the third catalyst bed; the reaction stream deflector 11 comprised a main axis 111 and a delivering element 112 extending spirally along the axial direction of the main axis, the inlet of the spirally extending flow channel formed by the delivering element 112 was located below the feed inlet 2 of the fresh alkene feedstock from the second branch pipeline 20 and the third branch pipeline 21. The reaction stream deflector 11 was arranged in the annular space between the central area where the catalyst delivery pipe 16 is located and the reactor wall.

In addition, three cone-shaped distribution baffles 12 (height: 0.1 m) arranged coaxially with catalyst delivery pipe 16, and three horizontal distribution baffles 13 (circular distribution plates) arranged below the cone-shaped distribution baffles 12 were each arranged between the first catalyst bed and the second catalyst bed and between the second catalyst bed and the third catalyst bed. The horizontal distribution baffle 13 was provided with holes through which the catalyst could pass, the holes of the horizontal distribution baffle 13 gradually became larger in the horizontally outward direction from the center of the axial moving bed reactor 1, the hole diameter of the largest hole was set to 25 mm, the hole diameter of the smallest hole was set to 5 mm. A bottom catalyst-collecting area 37 was provided at the lower part of the axial moving bed reactor 1.

The spent catalyst receiver 5, the catalyst regenerator 4 and the regenerated catalyst receiver 6 were successively arranged from top to bottom, catalyst circulation pipelines for connecting the spent catalyst receiver 5, the catalyst regenerator 4 and the regenerated catalyst receiver 6 were arranged vertically. The spent catalyst receiver 5, the catalyst regenerator 4 and the regenerated catalyst receiver 6 each had a diameter of 1200 mm and a straight-tube segment height of 6 m. The diameter of the stream circulation pipeline was 250 mm.

The fresh reaction feedstock is a mixture of isobutane, n-butane, butene and the like. The fresh feedstock feeding pipeline 17 was introduced, and then divided into three ways, each of which entered the corresponding catalyst bed 3.

The stream after entering each catalyst bed 3 and mixing had an alkane/alkene mole ratio of 700:1, the stream that circulated in the reactor had a flow velocity of 0.28 m/s, the total feed amount of the corresponding fresh feedstock was 482 kg/h, and the mixed alkene feedstock had a weight hourly space velocity of 0.25 $h^{-1}$.

The residence time of the catalyst in the axial moving bed reactor 1 was 72 hours.

The used catalyst was a FAU structure molecule sieve spherical catalyst with an average particle size of 1.8 mm. The preparation process thereof was as follows: an FAU structure NaY-type molecule sieve (produced by Sinopec Catalyst Company) was subjected to the ion exchange and the like to remove the sodium ion from the molecule sieve; then the molecule sieve was mixed uniformly with alumina in the weight ratio of 65:35; and the pellets was prepared via oil-ammonia column forming method and further dried and calcined to give the catalyst.

The reaction temperature in the axial moving bed reactor 1 was 70° C., and the reaction pressure was 2.5 MPa.

The fresh stream and the recycled stream were mixed, sent to the axial moving bed reactor 1 from the feed inlet 2, contacted with the catalyst filled in the first catalyst bed to perform the reaction, the stream after the reaction, obtained by the separation with the separation component 10, and the fresh stream from the first branch pipeline 19 were subjected to an intensified mixing with the deflector 11 and sent to the second catalyst bed to perform the reaction, the catalyst dispersed and falled down via the catalyst delivery pipe 16 and under the action of the catalyst distribution component to the downstream catalyst bed, and finally falled down to the bottom catalyst-collecting area 37. The catalyst obtained in the bottom catalyst-collecting area 37 was sent to the spent catalyst receiver 5 through the catalyst outlet. The first particle flow regulator 25 (L-type stream transportation valve set) was provided on the communication pipeline of the catalyst outlet of the axial moving bed reactor 1 and the catalyst inlet of the spent catalyst receiver 5, and the L-type stream transportation valve set was also communicated with a liquid-phase stream feeding pipeline to control the flow rate of the catalyst slurry (20 kg/h). Nitrogen gas was introduced into the spent catalyst receiver 5 to remove the liquid-phase stream carried in the catalyst, the liquid-phase stream was discharged through the outlet for withdrawing the liquid-phase stream 15, and a removed liquid filter 7 was arranged on the delivery pipeline for withdrawing the liquid-phase stream starting from the outlet for withdrawing the liquid-phase stream 15.

The liquid-withdrawn catalyst in the spent catalyst receiver 5 was introduced into the catalyst regenerator 4 for regeneration by using a mixed gas of nitrogen and air (the oxygen volume concentration was 1-21 vol %, adjusted from small to large, the superficial gas velocity was 0.1 m/s) as the high temperature deep regeneration medium of the catalyst, and high temperature (350-480° C., adjusted from small to large), the cycle of the normal pressure deep regeneration was 24 h, the mixed gas was introduced through the inlet for feeding the regeneration medium 30, the regeneration medium was discharged through the outlet for discharging the regeneration medium 31, the medium-after-regeneration filter 8 was arranged on the regeneration medium delivery pipeline starting from the outlet for discharging the regeneration medium 31. The catalyst regenerator 4 could also be provided with a fresh catalyst feed inlet for the fresh catalyst to enter the catalyst regenerator 4.

The regenerated catalyst would flow into the regenerated catalyst receiver 6 through the catalyst delivery pipeline at the bottom of the catalyst regenerator 4. The regenerated catalyst receiver 6 was provided with an inlet for supplementing the liquid-phase stream 32, a hydrocarbon-containing liquid-phase stream after the reaction was introduced to the regenerated catalyst receiver 6 through the inlet for supplementing the liquid-phase stream 32 to replace the gas in the gap of the catalyst, the obtained catalyst slurry was recycled to the top of the axial moving bed reactor 1. The second particle flow regulator 33 (L-type stream transportation valve set) was provided on the communication pipeline of the catalyst outlet of the regenerated catalyst receiver 6 and the catalyst inlet of the axial moving bed reactor 1, and the L-type stream transportation valve set is also communicated with a liquid-phase stream feeding pipeline to control the flow of the catalyst slurry (20 kg/h).

Example 2

Figure 3:
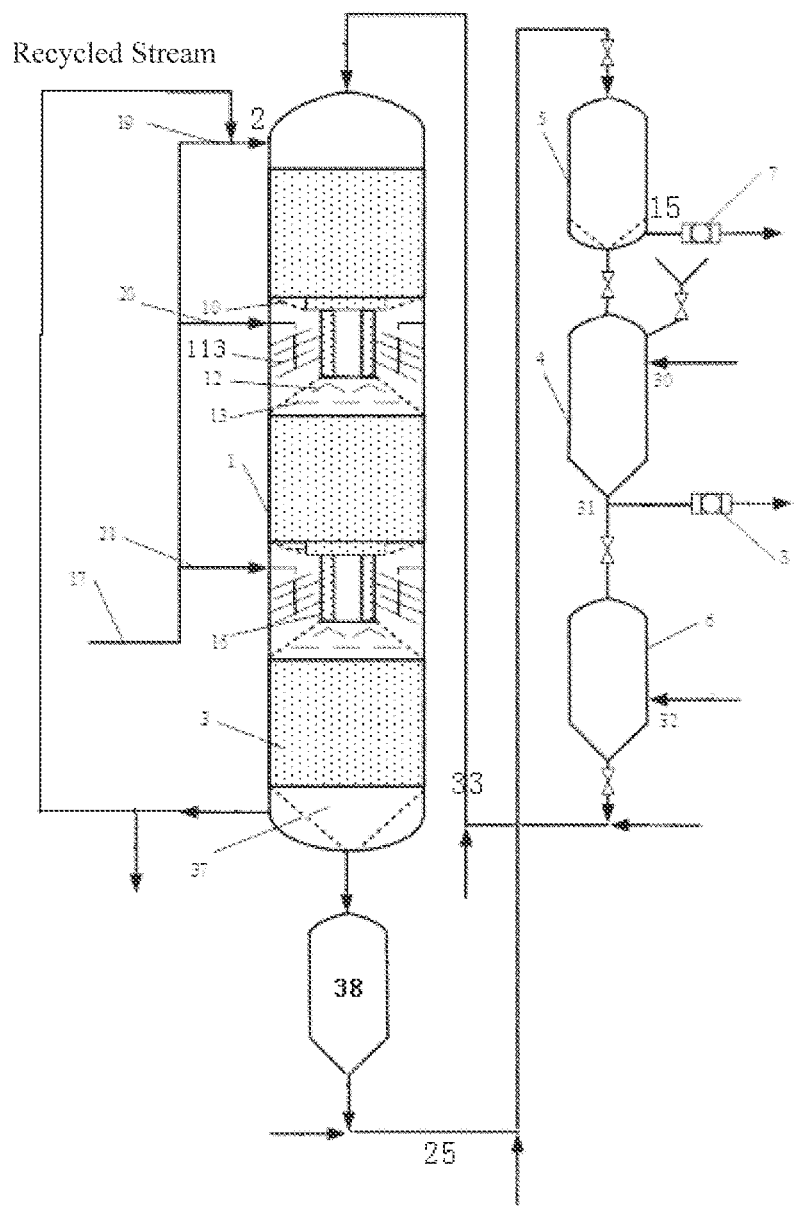
FIG. 3 shows a liquid-solid axial moving bed reaction and regeneration apparatus according to a specific embodiment provided by the present invention.

The solid acid alkylation reaction was performed with the apparatus as shown in FIG. 3. The difference from Example 1 was that this apparatus was further provided with a catalyst buffer tank 38 having a diameter of 500 mm and a straight-tube segment height of 4.2 m between the axial moving bed reactor 1 and the spent catalyst receiver 5.

In this example, the catalyst buffer tank 38 was added, which ensured that when the liquid-withdrawing operation was carried out in the spent catalyst receiver and/or when the operation of transferring the catalyst into the regenerator was carried out, the catalyst in the reactor still maintained the original speed and moved slowly downward. After the completion of the above operation(s), the catalyst accumulated in the catalyst buffer tank was gradually discharged to the spent catalyst receiver, which ensured the flow continuity of the catalyst stream in the axial moving bed reactor 1 and the smoothness of the apparatus operation.

Example 3

The solid acid alkylation reaction was carried out with the apparatus as shown in FIG. 1. The difference was as follows: the reaction stream deflector 11 as shown in FIG. 2 was replace with the reaction stream deflector 11 as shown in FIG. 1, the reaction stream deflector 11 comprised eight deflecting plates 113 arranged in a parallel and staggered manner with each other, the angle between the extension direction of the deflecting plate 113 and the horizontal plane was 25 degrees, the deflecting plates 113 were inclined upwards along the axial direction of the axial moving bed reactor 1, four deflecting plates 113 were fixedly connected to the wall of the axial moving bed reactor 1, four deflecting plates 113 were fixedly connected to the wall of the catalyst delivery pipe 16, the distance between adjacent deflecting plates 113 was 25 mm.

Example 4

This example was carried out in the liquid-solid axial moving bed reactor as shown in FIG. 4, wherein the used spent catalyst receiver, the used catalyst regenerator, and the used regenerated catalyst receiver and other equipments not mentioned herein were identical or similar to those in Example 1.

The axial moving bed reactor had a shell inner diameter of 600 mm, and included two reaction beds and two regenerated catalyst beds that were intervally successively arranged, each bed had a height of 1.8 m.

The regeneration medium outlet arranged at the top of the catalyst regeneration bed was positioned at 85% of the catalyst regeneration bed from bottom to top, and the regeneration medium inlet was positioned at 5% of the catalyst regeneration bed from bottom to top. The outlet of the inserted-type conduit was positioned at 80% of the catalyst regeneration bed from bottom to top.

The fresh reaction feedstock was identical to that used in Example 1. After feeding from the fresh feedstock feeding pipeline, the feedstock was divided into two ways and mixed with the recycled stream or the liquid-phase stream after the upstream reaction and then each entered the corresponding reaction bed.

After mixing, the molar ratio of alkanes to alkenes in the distribution zone of the reactor was 700±100:1, and the weight hourly space velocity of the mixed alkene feedstock was 0.25 $h^{-1}$.

The same catalyst as in Example 1 was used.

The reaction temperature in the reaction bed was 70° C., and the reaction pressure was 2.5 MPa.

In the catalyst regeneration bed, the liquid-phase stream after the reaction, containing a part of alkylation oils and in which hydrogen is dissolved, was used as the regeneration medium of the catalyst. The regeneration conditions such as temperature and pressure were similar to the reaction conditions such as temperature and pressure.

The total residence time of the catalyst in the axial moving bed reactor was controlled to 168 h.

The catalyst that finally lost its activity was introduced into the high-temperature deep regeneration system. The deep regeneration was performed at the regeneration temperature of 280° C. and the regeneration pressure of 2.5 MPa with hydrogen gas containing some low-carbon hydrocarbons to completely restore the catalyst activity.

After the activity was restored, the catalyst was reintroduced to the fresh catalyst feed inlet at the top of the reactor to continue to participate in the reaction, and the process is circulated in this manner.

Comparative Example 1

The solid acid alkylation reaction was carried out on a medium-sized test apparatus containing two fixed beds connected in parallel. The specific operation process was as follows: when the first reactor was in the alkylation reaction, the second reactor carried out the high-temperature deep regeneration operation, and the two fixed bed reactors connected in parallel were switched for use, so that the apparatus could be continuously and stably operated. Each fixed bed type reactor had an inner diameter of 200 mm and a height of 2500 mm. The preparation process of the catalyst filled in the reactor was the same as that in Example 1, except that the diameter of the pellet was 2.7 mm, the filling amount was 28 kg, and the filling height was 1500 mm. The reaction feedstock was the same as in Example 1, the molar ratio of alkane to alkene in the reactor was 800:1, the feed amount of the fresh mixed alkenes was 6.3 kg/h, and the weight hourly space velocity was 0.09 $h^{-1}$ relative to the alkene. The catalyst in the bed needed a high-temperature deep regeneration once every 24 hours. The temperature of the mixed gas of nitrogen and air (identical to Example 1) was increased to 480° C. from normal temperature, the catalyst in the bed was subjected to a high-temperature oxidation regeneration for 3 hours under normal pressure, the bed layer needed to be cooled after regeneration, and the whole regeneration period was 24 hours. After the regeneration was finished, the streams in the reactor in the reaction state were returned to the reactor in which the catalyst had been regenerated, the alkylation reaction experiment was continued with the regenerated catalyst, and the reactor in which the reaction streams had been evacuated was switched to the regeneration operation, the process was circulated in this manner.

After the continuous stable operation of the apparatuses of the above examples and comparative example for 1000 hours, the obtained alkylation oil was measured and the test results were shown in Table 1.

TABLE 1

|  | RON | MON | Alkene $C_5^+$ Yield | TMP/ DMH | $C_9^+$ Product wt % | Catalyst residence time |
| --- | --- | --- | --- | --- | --- | --- |
| Example 1 | 95.5 | 91.5 | 1.99 | 3.53 | 5.12 | 72 h |
| Example 2 | 95.8 | 92.0 | 2.0 | 3.62 | 5.08 | 72 h |

TABLE 1-continued

|  | RON | MON | Alkene C5+ Yield | TMP/ DMH | C9+ Product wt % | Catalyst residence time |
|---|---|---|---|---|---|---|
| Example 3 | 95.7 | 97.0 | 2.0 | 3.60 | 5.11 | 72 h |
| Example 4 | 95.6 | 91.5 | 1.99 | 3.55 | 5.13 | 168 h |
| Comparative Example 1 | 95.2 | 91.3 | 1.96 | 3.24 | 6.76 | 24 h |

As can be seen from Table 1, the octane number of the alkylation oil obtained by using the solid acid alkylation process or apparatus provided by the present invention was slightly better than that of the fixed bed technology, the alkene yield in the alkylation oil was higher, the target product (trimethylpentane) selectivity was higher, and the yield of the C9+ product was lower.

Compared with Example 1, Example 2 with the catalyst buffer tank had better product yield and target product selectivity.

From the view of the apparatus operation, for the fixed bed alkylation technology, in order to realize the continuous and stable operation of the reaction apparatus, at least two or more reactors were required to be switched (e.g., Comparative Example 1). The catalyst in the bed was regenerated at high temperature at regular intervals (24 hours), and it was necessary to cool the high temperature bed after the deep regeneration. Since the apparatus was frequently switched between the reaction temperature and the regeneration temperature, a plurality of problems were caused in the continuous and stable operation in industrial application. But the apparatus and the process provided by the invention can meet the requirements with a single (set of) equipment. The investment cost of the apparatus was reduced. In addition, the inactivated catalyst particles were led out of the liquid-solid axial moving reactor to carry out the deep regeneration, under the premise of not influencing the stable operation of the reaction apparatus, the continuous operation of the reaction with catalyst and the catalyst regeneration was realized, the stable equilibrium activity of the catalyst in the apparatus was maintained, the selectivity of the target product in the alkylation oil was improved.

In particular, as can be seen from Example 4, the octane number of the alkylation oil obtained by the axial moving bed technology, in which the reaction bed and the catalyst regeneration bed were intervally successively arranged, was slightly superior to that of the fixed bed technology, the yield of the alkene in the alkylation oil was higher, the target product (trimethylpentane) selectivity was higher, the yield of the C9+ product was lower, and the residence time of the catalyst was prolonged to one week, indicating that the axial moving bed technology, in which the reaction bed and the catalyst regeneration bed were intervally successively arranged, had higher technical superiority. The deactivated catalyst particles were led out of the reactor for deep regeneration, so that the continuous operation of the reaction with catalyst and the catalyst regeneration was realized on the premise of not influencing the stable operation of the reaction apparatus. The relatively stable equilibrium activity of the catalyst in the apparatus was maintained, the selectivity of the target product in the alkylation oil and the operation flexibility of the apparatus were improved, the high-temperature deep regeneration frequency of the catalyst was reduced, and the economic competitiveness of the apparatus was improved.

Therefore, the axial moving bed solid acid alkylation technology provided by the present invention has better industrial application prospects.

The preferred embodiments of the present invention have been described above in detail, but the present invention is not limited thereto. Within the scope of the technical concept of the present invention, various simple modifications can be made to the technical solutions of the present invention, including the combinations of various technical features in any other suitable manner. These simple modifications and combinations should also be regarded as the disclosed content of the present invention, and all belong to the protection scope of the present invention.

The invention claimed is:

1. A liquid-solid axial moving bed reaction and regeneration apparatus, which is characterized in that the apparatus comprises:
    an axial moving bed reactor, a spent catalyst receiver, a catalyst regenerator and a regenerated catalyst receiver that are successively connected, wherein, a catalyst outlet of the regenerated catalyst receiver is communicated with a catalyst inlet of the axial moving bed reactor;
    wherein, the axial moving bed reactor is provided with at least two catalyst beds that are arranged up and down, the axial moving bed reactor is provided with a feed inlet above each catalyst bed;
    a catalyst delivery pipe is arranged between two adjacent catalyst beds so that the catalyst can move from top to bottom in the axial moving bed reactor;
    the axial moving bed reactor further comprises at least one catalyst regeneration bed;
    the axial moving bed reactor has a catalyst inlet, which is communicated with the top of the first catalyst bed;
    a catalyst inlet and a reaction stream inlet are arranged at the top of each catalyst bed, wherein the catalyst inlet of the first reaction bed is the catalyst inlet of the axial moving bed reactor, the catalyst inlet of the subsequent reaction bed is communicated with the catalyst delivery pipe;
    a catalyst outlet communicated with the catalyst delivery conduit and a reaction stream outlet are arranged at the bottom of each catalyst bed;
    a catalyst inlet communicated with the catalyst delivery conduit and a regeneration medium outlet are arranged at the top of the catalyst regeneration bed;
    a catalyst outlet communicated with the catalyst delivery conduit and a regeneration medium inlet are arranged at the bottom of the catalyst regeneration bed;
    an isolation medium inlet is arranged on the catalyst delivery pipeline for transferring the catalyst from the catalyst regeneration bed to the catalyst bed;
    a separation component is arranged at the bottom of each catalyst bed;
    various beds are communicated with each other through the catalyst delivery pipeline;
    the bottom of the catalyst bed and the regeneration bed are communicated by means of a catalyst delivery conduit that is inserted into the interior of the regeneration bed, and the outlet of the inserted-type catalyst delivery conduit is below the regeneration medium outlet in the regeneration bed;
    the isolation medium inlet and the reaction stream outlet of the last catalyst bed are communicated so that the reaction stream is pressurized with a pump and then used as the isolation medium;

the reaction stream outlet of the upstream catalyst bed is communicated with an inlet for feeding the reaction stream of the downstream catalyst bed, optionally by means of a communication pipeline, and a fresh reaction feedstock inlet can also be arranged on the communication pipeline;

the regeneration medium outlet of an upstream catalyst regeneration bed can be communicated with the regeneration medium inlet of a downstream catalyst regeneration bed by means of a pipeline;

a separation component is provided between two adjacent catalyst beds, and if the catalyst regeneration bed is present as the last bed, a separation component is provided between an upstream catalyst bed and the last catalyst regeneration bed, wherein the inside space of the separation component is communicated with the catalyst delivery pipe, the separation component is for separating a catalyst from a stream after the reaction in the upstream catalyst bed, and the catalyst obtained by the separation with the separation component moves down through the catalyst delivery pipe.

2. The liquid-solid axial moving bed reaction and regeneration apparatus according to claim 1, wherein a reaction stream outlet of the last catalyst bed of the axial moving bed reactor is communicated with the feed inlet of the first catalyst bed of the axial moving bed reactor to recycle the reaction stream obtained from the axial moving bed reactor back to the axial moving bed reactor.

3. The liquid-solid axial moving bed reaction and regeneration apparatus according to claim 1, wherein a reaction stream deflector is provided between two adjacent catalyst beds and if any, a reaction deflector is provided between an upstream catalyst bed and the last catalyst regeneration bed, and the reaction stream deflector is for intensifying the mixing of the stream after the reaction and the liquid-state fresh reaction feedstock fed from the feed inlet.

4. The liquid-solid axial moving bed reaction and regeneration apparatus according to claim 3, wherein, the reaction stream deflector comprises a main axis and a delivering element extending spirally along the axial direction of the main axis.

5. The liquid-solid axial moving bed reaction and regeneration apparatus according to claim 3, wherein the reaction stream deflector comprises a plurality of deflecting plates, wherein the deflecting plates are inclined along the axial direction of the axial moving bed reactor, and arranged in a staggered manner with each other to form a flow channel through which the reaction stream can pass.

6. The liquid-solid axial moving bed reaction and regeneration apparatus according to claim 1, wherein a catalyst distribution component is arranged between two adjacent catalyst beds and if a catalyst regeneration bed is present in the axial moving bed reactor, between two adjacent beds, wherein the catalyst distribution component is for dispersing the catalyst at the outlet of the catalyst delivery pipe.

7. The liquid-solid axial moving bed reaction and regeneration apparatus according to claim 6, wherein the catalyst distribution component comprises a cone-shaped distribution baffle, and the cone-shaped distribution baffle is arranged coaxially with the catalyst delivery pipe.

8. The liquid-solid axial moving bed reaction and regeneration apparatus according to claim 7, wherein the number of the cone-shaped distribution baffle is identical to that of the catalyst delivery pipe.

9. The liquid-solid axial moving bed reaction and regeneration apparatus according to claim 7, wherein the catalyst distribution component further comprises a horizontal distribution baffle arranged below the cone-shaped distribution baffle, and the horizontal distribution baffle is provided with holes through which the catalyst can pass.

10. The liquid-solid axial moving bed reaction and regeneration apparatus according to claim 1, wherein the catalyst regenerator is provided with a fresh catalyst feed inlet for the fresh catalyst to enter the catalyst regenerator.

11. The liquid-solid axial moving bed reaction and regeneration apparatus according to claim 1, wherein a spent catalyst receiver, a catalyst regenerator and a regenerated catalyst receiver are successively arranged from top to bottom, and catalyst circulation pipelines for connecting the spent catalyst receiver, the catalyst regenerator and the regenerated catalyst receiver are arranged vertically or inclined at an angle relative to the horizontal plane of not less than 40 degrees.

12. The liquid-solid axial moving bed reaction and regeneration apparatus according to claim 1, wherein a first particle flow regulator is arranged on the communication pipeline of the catalyst outlet of the axial moving bed reactor and the catalyst inlet of the spent catalyst receiver; and a second particle flow regulator is arranged on the communication pipeline of the catalyst outlet of the regenerated catalyst receiver and the catalyst inlet of the axial moving bed reactor;

the first particle flow regulator and the second particle flow regulator each independently are an L-shaped or approximately L-shaped stream transportation valve set.

13. The liquid-solid axial moving bed reaction and regeneration apparatus according to claim 1, wherein the apparatus further comprises a catalyst buffer tank, the catalyst buffer tank is arranged between the axial moving bed reactor and the spent catalyst receiver, the catalyst inlet of the catalyst buffer tank is communicated with the catalyst outlet of the axial moving bed reactor, and the catalyst outlet of the catalyst buffer tank is communicated with the catalyst inlet of the spent catalyst receiver.

14. A solid acid alkylation process, wherein the process is performed in the liquid-solid axial moving bed reaction and regeneration apparatus according to claim 1, and the liquid-phase feedstock is sent into the axial moving bed reactor from the feed inlet above each catalyst bed and contacted with the catalyst to perform the reaction.

15. The process according to claim 14, wherein the process further comprises: the reaction product obtained at the bottom of the axial moving bed reactor is recycled to a position above the uppermost upstream catalyst bed and mixed with the liquid-phase feedstock and then fed into the reactor.

16. The process according to claim 14, wherein in the axial moving bed reactor, the reaction temperature is 30-100° C., and the pressure is 1-3.4 MPa;

the weight hourly space velocity of the stream entering each catalyst bed based on the alkene is 0.05-1 $h^{-1}$;
the molar ratio of isoalkane to alkene in the stream entering each catalyst bed is 200-1000:1;
and the residence time of the catalyst in the axial moving bed reactor is 6-72 h.

17. The process according to claim 14, wherein the catalyst is a solid acid catalyst, the solid acid catalyst contains a molecule sieve and a heat-resistant inorganic oxide, wherein based on the total amount of the solid acid catalyst, the content of the molecule sieve is 65-95 wt %, the content of the heat-resistant inorganic oxide is 5-35 wt %;

the molecule sieve is selected from at least one of FAU structure zeolite, BETA structure zeolite and MFI structure zeolite, the heat-resistant inorganic oxide is alumina and/or silica;

the solid acid catalyst further contains a metal active component, the metal active component is selected from at least one of Fe, Co, Ni, Pd and Pt, and based on the total amount of the solid acid catalyst, the content of the metal active component is in a range of 0.15-2 wt %.

18. The process according to claim 14, wherein between two adjacent catalyst beds is provided a separation component, the inside space of the separation component is communicated with the catalyst delivery pipe, the separation component is for separating the stream after the reaction in the upstream catalyst bed from the catalyst, and the catalyst obtained by the separation with the separation component moves down through the catalyst delivery pipe.

19. The process according to claim 14, wherein a reaction stream deflector is provided between two adjacent catalyst beds and the reaction stream deflector is for intensifying the mixing of the stream after the reaction and the liquid-state fresh reaction feedstock fed from the feed inlet.

20. The process according to claim 19, wherein the reaction stream deflector comprises a main axis and a delivering element extending spirally along the axial direction of the main axis.

21. The process according to claim 19, wherein the reaction stream deflector comprises a plurality of deflecting plates, wherein the deflecting plates are inclined along the axial direction of the axial moving bed reactor, and arranged in a staggered manner with each other to form a flow channel through which the reaction stream can pass.

22. The process according to claim 14, wherein a catalyst distribution component is arranged between two adjacent catalyst beds, which is for dispersing the catalyst at the outlet of the catalyst delivery pipe.

23. The process according to claim 22, wherein the catalyst distribution component comprises a cone-shaped distribution baffle, and the cone-shaped distribution baffle is arranged coaxially with the catalyst delivery pipe.

24. The process according to claim 23, wherein the number of the cone-shaped distribution baffle is identical to that of the catalyst delivery pipe.

25. The process according to claim 22, wherein the catalyst distribution component further comprises a horizontal distribution baffle arranged below the cone-shaped distribution baffle, and the horizontal distribution baffle is provided with holes through which the catalyst can pass.

26. The process according to claim 14, wherein the catalyst at the bottom of the axial moving bed reactor is transported to the spent catalyst receiver to remove the liquid-phase stream carried in the catalyst, and then transported to the catalyst regenerator for regeneration.

27. The process according to claim 26, wherein the superficial flow velocity of the regeneration medium in the catalyst regenerator is in a range of 0.003-0.8 m/s.

28. The process according to claim 27, wherein the superficial flow velocity of the regeneration medium in the catalyst regenerator is in a range of 0.02-0.5 m/s.

29. The process according to claim 14, wherein the catalyst regenerator is provided with a fresh catalyst feed inlet for the fresh catalyst to enter the catalyst regenerator.

30. The process according to claim 14, wherein a spent catalyst receiver, a catalyst regenerator and a regenerated catalyst receiver are successively arranged from top to bottom, and catalyst circulation pipelines for connecting the spent catalyst receiver, the catalyst regenerator and the regenerated catalyst receiver are arranged vertically or inclined at an angle relative to the horizontal plane of not less than 40 degrees.

31. The process according to claim 14, wherein a first particle flow regulator is arranged on the communication pipeline of the catalyst outlet of the axial moving bed reactor and the catalyst inlet of the spent catalyst receiver; and a second particle flow regulator is arranged on the communication pipeline of the catalyst outlet of the regenerated catalyst receiver and the catalyst inlet of the axial moving bed reactor;

the first particle flow regulator and the second particle flow regulator each independently are an L-shaped or approximately L-shaped stream transportation valve set.

32. The process according to claim 14, wherein the apparatus further comprises a catalyst buffer tank, the catalyst buffer tank is arranged between the axial moving bed reactor and the spent catalyst receiver, the catalyst inlet of the catalyst buffer tank is communicated with the catalyst outlet of the axial moving bed reactor, and the catalyst outlet of the catalyst buffer tank is communicated with the catalyst inlet of the spent catalyst receiver.

33. The process according to claim 14, wherein the axial moving bed reactor is provided with a catalyst regeneration bed, which is located below a reaction bed, and the catalyst leaving the reaction bed enters the catalyst regeneration bed, and is regenerated in the presence of a liquid hydrocarbon in which hydrogen is dissolved; wherein:

the regeneration conditions in the catalyst regeneration bed comprise:

the regeneration temperature is in a range of 50-140° C., the superficial flow velocity of the regeneration medium in the regenerator is in a range of 0.01-0.5m/s;

the regeneration medium is a liquid hydrocarbon in which hydrogen is dissolved;

the liquid hydrocarbon is C3-C6 saturated alkane or a mixture of the reaction product and the saturated alkane.

34. The process according to claim 33, wherein the liquid hydrocarbon is a mixture of C3-C6 saturated alkane and the reaction product.

35. The liquid-solid axial moving bed reaction and regeneration apparatus according to claim 1, wherein the number of the catalyst bed and the number of the catalyst regeneration bed are identical and the catalyst bed and the catalyst regeneration bed are intervally successively arranged.

36. The liquid-solid axial moving bed reaction and regeneration apparatus according to claim 1, wherein the number of the catalyst regeneration bed is one less than the number of the catalyst bed, the catalyst bed and the catalyst regeneration bed are intervally successively arranged, and the catalyst reaction beds are arranged both at the top and the bottom of the axial moving bed reactor.

* * * * *

UNITED STATES PATENT AND TRADEMARK OFFICE
CERTIFICATE OF CORRECTION

PATENT NO. : 11,912,643 B2
APPLICATION NO. : 17/287648
DATED : February 27, 2024
INVENTOR(S) : Lifeng Hu et al.

It is certified that error appears in the above-identified patent and that said Letters Patent is hereby corrected as shown below:

In the Claims

In Claim 17, Column 44, Line 67, "heat- resistant" should read --heat-resistant--.

Signed and Sealed this
Fourth Day of June, 2024

Katherine Kelly Vidal
*Director of the United States Patent and Trademark Office*